(12) United States Patent
Cui et al.

(10) Patent No.: US 8,506,726 B2
(45) Date of Patent: Aug. 13, 2013

(54) ENDOSCOPE REPROCESSOR

(75) Inventors: Shengfu Cui, Ashigara-kami-gun (JP); Mitsuhiko Serizawa, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 650 days.

(21) Appl. No.: 12/192,647

(22) Filed: Aug. 15, 2008

(65) Prior Publication Data

US 2009/0044845 A1    Feb. 19, 2009

(30) Foreign Application Priority Data

Aug. 16, 2007 (JP) ................................. 2007-212266
Sep. 6, 2007 (JP) ................................. 2007-231229

(51) Int. Cl.
  *B08B 13/00* (2006.01)
(52) U.S. Cl.
  USPC ......... 134/56 R; 134/57 R; 134/137; 134/200
(58) Field of Classification Search
  USPC ................. 134/56 R, 57 R, 137, 200, 201
  See application file for complete search history.

(56) References Cited

U.S. PATENT DOCUMENTS

| | | | | |
|---|---|---|---|---|
| 4,805,826 | A * | 2/1989 | Moriki et al. | 228/18 |
| 5,425,815 | A * | 6/1995 | Parker et al. | 134/26 |
| 5,682,710 | A * | 11/1997 | Davies et al. | 49/162 |
| 5,840,251 | A | 11/1998 | Iwaki | |
| 7,479,257 | B2 | 1/2009 | Nguyen et al. | |
| 2002/0001537 | A1 * | 1/2002 | Hlebovy et al. | 422/28 |
| 2002/0159917 | A1 | 10/2002 | Swart et al. | |
| 2004/0101456 | A1 * | 5/2004 | Kuroshima et al. | 422/297 |
| 2009/0065034 | A1 * | 3/2009 | Suzuki et al. | 134/56 R |
| 2009/0217956 | A1 * | 9/2009 | Noguchi et al. | 134/57 R |

FOREIGN PATENT DOCUMENTS

| | | |
|---|---|---|
| CN | 1920530 A | 2/2007 |
| EP | 0 945 140 A2 | 9/1999 |
| EP | 0 986 988 A1 | 3/2000 |
| EP | 1 757 313 A1 | 2/2007 |
| GB | 1168035 | 10/1969 |
| JP | 64-070021 A | 3/1989 |
| JP | 07-079907 A | 3/1995 |
| JP | 07-111981 A | 5/1995 |
| JP | 09-164117 A | 6/1997 |
| JP | 10-305011 A | 11/1998 |
| JP | 11-076140 A | 3/1999 |
| JP | 11-113840 A | 4/1999 |
| JP | 2003-135396 A | 5/2003 |
| JP | 2006-068095 A | 3/2006 |
| WO | 2006/115177 A1 | 11/2006 |
| WO | WO 2007007482 A1 * | 1/2007 |

OTHER PUBLICATIONS

EP Communication, dated Jan. 27, 2009, issued in corresponding EP Application No. 08144471.0, 9 pages.

(Continued)

*Primary Examiner* — Michael Barr
*Assistant Examiner* — Benjamin L Osterhout
(74) *Attorney, Agent, or Firm* — Sughrue Mion, PLLC

(57) ABSTRACT

The endoscope reprocessor includes a basin for receiving an endoscope to be reprocessed, a rack which secures thereto a portion of the endoscope and moves vertically within the basin, a drive unit for vertically moving the rack, a positioning member for adjusting a rack stopping position when the endoscope is to be set on the rack and a drive control unit for controlling the drive unit based on computed results from the positioning member.

9 Claims, 16 Drawing Sheets

(56) References Cited

OTHER PUBLICATIONS

Notification of Reasons for Refusal, dated Jan. 4, 2012, issued in corresponding JP Application No. 2007-212266, 4 pages in English and Japanese.

Notification of Reasons for Refusal, dated Feb. 7, 2012, issued in corresponding JP Application No. 2007-231229, 4 pages in English and Japanese.

First Office Action, dated Jun. 1, 2012, issued in corresponding CN Application No. 200810145949.5, 13 pages in English and Chinese.

* cited by examiner

ENDOSCOPE REPROCESSOR

The entire contents of all documents cited in this specification are incorporated herein by reference.

BACKGROUND OF THE INVENTION

The present invention relates to an endoscope reprocessor for the automated reprocessing of an endoscope. In particular, the present invention relates to an endoscope reprocessor having a rack for holding an endoscope. The invention also relates to an endoscope reprocessor which minimizes the degradation and consumption of disinfectant and is able to shorten the reprocessing time.

In the present specification, "reprocessing" an endoscope refers to performing a cleaning and disinfecting process on an endoscope, which process includes specifically a step for cleaning an endoscope with a liquid detergent (cleaning step), a step for disinfecting with a liquid disinfectant the endoscope that has been cleaned with detergent (disinfecting step), and a step for rinsing the endoscope that has been disinfected with disinfectant (rinsing step). The term "cleaning" refers to the cleansing or washing of an endoscope with a liquid detergent that is carried out in the cleaning step.

As is commonly known, the endoscope is an instrument used to insert a tube into the human body or another living body and carry out diagnosis, sample collection and treatment within the body, particularly on internal organs.

The endoscope is basically composed of an insertion tube which is inserted into the body, a control unit for controlling the insertion tube and for controlling air and water supply, etc. in the endoscope, a connector which connects to an air supply and suction pump (light guide (LG) connector), and a universal cord (LG soft portion) which connects the connector with the control unit and the insertion tube.

Endoscopes are generally not disposable, single-use devices; rather, they are used repeatedly and on more than one patient. For an endoscope to be repeatedly used in this way, it must be meticulously reprocessed after each use in order to prevent endoscopically transmitted bacterial infections. To this end, various types of endoscope reprocessors for the automated reprocessing of endoscopes have been developed for commercial use.

Such apparatuses for reprocessing endoscopes include, for example, the endoscope reprocessor described in JP 2003-135396 A.

JP 2003-135396 A describes an apparatus for reprocessing an endoscope inside a basin, which apparatus is characterized by having a tray which is insertably disposed at the interior of the basin and on which the endoscope is set. The reprocessor of JP 2003-135396 A is used to reprocess an endoscope by setting the endoscope on the tray outside of the basin, inserting the tray into the basin, and circulating liquid detergent and liquid disinfectant inside the basin.

Another example of a known endoscope reprocessor is the apparatus disclosed in JP 2006-68095 A wherein, after the insertion tube and the universal cord of the endoscope have been coiled and the endoscope has been placed in a basin, the endoscope is reprocessed by circulating liquid detergent and liquid disinfectant over a pathway that includes the basin (or by immersion only in the case of the disinfectant).

Such an endoscope reprocessor generally reprocesses an endoscope by carrying out a cleaning step in which the endoscope is cleaned with a liquid detergent and may also be rinsed with water, a disinfecting step in which the endoscope is disinfected with a liquid disinfectant, and a rinsing step in which the endoscope is rinsed with water such as tap water to remove disinfectant and the like.

JP 10-305011 A discloses an endoscope reprocessor which reprocesses only the insertion tube of the endoscope. The insertion tube is placed in a tubular main body of the reprocessor, following which a cleaning step that involves rinsing with water and the use of a liquid detergent and a disinfecting step that involves the use of a liquid disinfectant are carried out, after which drying is carried out by the passage of pressurized air.

In the respective steps carried out in an endoscope reprocessor, i.e., the cleaning step, disinfecting step and rinsing step, reprocessing is carried out by circulating the reprocessing liquids not only over the exterior of the endoscope, but also inside the channels at the interior of the endoscope, such as the forceps channel and the air/water channel.

Owing to the difficulty of discharging liquids from these channels inside the endoscope, after reprocessing is finished, the reprocessing liquids are forced out by introducing air into the channels. Once reprocessing is completed, reprocessing liquids remaining inside the basin which houses the endoscope are drained from the basin gravitationally or with a drain pump.

SUMMARY OF THE INVENTION

As indicated in JP 2003-135396 A, the automated reprocessing of endoscopes can be carried out by cleaning and disinfecting endoscopes with an endoscope reprocessor. Moreover, by setting the endoscope on a tray beforehand, the time required to set the endoscope in the reprocessor can be shortened.

However, in the endoscope reprocessor described in JP 2003-135396 A, the tray must be removed from the basin. As a result, the operator has to carry the tray to and from the endoscope reprocessor, which increases the work required of the operator.

Also, in endoscope reprocessors, the liquid disinfectant is generally recovered and reused for a predetermined number of reprocessing cycles.

Yet, following the end of a step, because the reprocessing liquid within the basin is merely drained from the basin, residual reprocessing liquid remains within the basin and on the outer surface of the endoscope. As a result, when liquid disinfectant is fed into the basin following completion of the cleaning step, reprocessing liquid from the cleaning step (detergent or water used for rinsing) mixes with the disinfectant, diluting the disinfectant and thus lowering its potency. In addition, even when the disinfectant is discharged from the basin and collected following completion of the disinfecting step, because some disinfectant remains in the basin and ends up being discharged together with rinsing liquid in the subsequent rinsing step, the amount of liquid disinfectant decreases with each reprocessing cycle. The result is an increased consumption of liquid disinfectant.

Also, in conventional endoscope reprocessors, time is set aside in each step to allow liquids to drain out following liquid discharge from the basin, which ends up extending the endoscope reprocessing time.

Therefore, a first object of the invention is to resolve the above problems associated with the prior art by providing an endoscope reprocessor which enables the operator to easily and efficiently set an endoscope in place for reprocessing.

A second object of the invention is to resolve the foregoing problems in the prior art by providing an endoscope reprocessor for cleaning and disinfecting an endoscope by carrying out a cleaning step, a disinfecting step and a rinsing step, which reprocessor reduces the amount of reprocessing liquids such as detergent and disinfectant remaining inside the basin and on the endoscope outer surface following the discharge of liquids from the basin at the completion of each step, thus minimizing the degradation and loss of reprocessing liquids such as detergent and disinfectant, and also shortens the reprocessing time.

In order to achieve the first aspect, a first aspect of the invention provides an endoscope reprocessor comprising:

a basin for receiving an endoscope to be reprocessed;

a rack which secures thereto a portion of the endoscope and moves vertically within the basin;

a drive unit for vertically moving the rack;

a positioning member for adjusting a rack stopping position when the endoscope is to be set on the rack; and a drive control unit for controlling the drive unit based on computed results from the positioning member.

In the endoscope reprocessor according to the first aspect of the invention, it is preferred for the basin to have a horizontal cross-section which is rectangular and to have a vertical height which is greater than a length of the horizontal cross-section in a lengthwise direction thereof.

Preferably, the endoscope reprocessor further comprises a reading unit for reading operator identifying information, and the positioning member selects the rack stopping position based on the identifying information read by the reading unit.

The reading unit preferably reads the identifying information wirelessly.

The drive unit preferably tilts the rack to a predetermined angle at the rack stopping position.

The rack preferably secures the endoscope thereto at a plurality of places.

The rack preferably has locking members which respectively secure thereto a connector and a control unit of the endoscope.

Preferably, the rack additionally has a locking member which secures thereto an insertion tube of the endoscope.

Preferably, the endoscope reprocessor further comprises, in addition to the basin, at least one additional basin of the same construction, and the at least one additional basin has a horizontal cross-section which is rectangular and the basin and the at least one additional basin are arranged in parallel with long sides of the respective rectangular cross-sections thereof facing frontally so as to be mutually adjacent.

In order to achieve the second object, a second aspect of the invention provides an endoscope reprocessor comprising:

a basin for receiving an endoscope to be reprocessed;

a lid for the basin; and a blowing unit for blowing a gas into the basin, wherein the reprocessor is adapted for carrying out a process for cleaning and disinfecting the endoscope, the process comprising a cleaning step for cleaning the endoscope with a liquid detergent, a disinfecting step for disinfecting the endoscope cleaned with the liquid detergent and a rinsing step for rinsing the disinfected endoscope, and wherein the blowing unit blows the gas into the basin each time the cleaning step, the disinfecting step or the rinsing step ends.

Preferably, the endoscope reprocessor according to the second aspect of the invention further comprises a control unit for controlling a cleaning and disinfecting process, and the control unit controls the cleaning and disinfecting process so as to carry out, in order, the cleaning step, the disinfecting step and the rinsing step, and also controls the blowing unit so as to blow the gas into the basin each time the cleaning step, the disinfecting step or the rinsing step ends.

Preferably, the basin has a bottom surface inclined in one direction for receiving the endoscope, and the blowing unit has a plurality of nozzles arrayed in a direction of inclination of the bottom surface of the basin.

Preferably, the plurality of nozzles sequentially begin blowing the gas into the basin, starting with one of the plurality of nozzles situated highest on the bottom surface of the basin.

Preferably, the basin has a holding member for holding the endoscope capable of being raised to emerge from and being lowered to be received within the basin and, following completion of the rinsing step, the blowing unit blows the gas into the basin as the holding member is being raised.

The blowing unit preferably blows the gas onto inner surfaces of the basin, outer surfaces of the endoscope received within the basin, and an underside of the lid.

The blowing unit is preferably variable in gas blowing direction.

Preferably, the endoscope reprocessor according to the second aspect of the invention further comprises a supply unit for supplying the gas to a channel lumen within the endoscope, and the gas is blown from the blowing unit into the basin by switching between a path for gas supply to the channel lumen and a path for gas supply to the blowing unit.

The endoscope reprocessor according to the first aspect of the invention, by virtue of the above-described arrangement, enables the endoscope to be set on the rack on site without having to carry the rack to and from the reprocessor. Moreover, by using a drive mechanism to adjust the rack height, work can be carried out at a desired height, thus enabling the endoscope to be set on the rack easily and in a short time.

Another advantage of the same aspect of the invention is that, the rack is tilted to a predetermined angle at the endoscope loading position, further facilitating the setting of the endoscope on the rack.

A further advantage of the same aspect of the invention is that disposing a plurality of basins with the long sides in the horizontal direction thereof facing each other enables a plurality of endoscopes to be cleaned. Also, giving the basins a vertically elongated construction adapted to vertical movement of the rack allows the endoscopes to be easily loaded into the reprocessor and enables the reprocessor to be downsized.

A still further advantage of the same aspect of the invention is that providing the rack with locking members for securing the control unit and connector of the endoscope to the rack enables the endoscope to be more easily and efficiently set on the rack.

An additional advantage of the same aspect of the invention is that, by securing predetermined portions of the endoscope with the locking members, portions of the endoscope other than those which are secured can be placed in a state of non-contact with the rack, enabling the surface area of contact between the rack and the endoscope to be reduced. Moreover, the position of the endoscope within the basin can be fixed, enabling the endoscope to be efficiently cleaned and disinfected.

The endoscope reprocessor according to the second aspect of the invention, by virtue of the above-described arrangement, uses a blowing unit to blow a gas such as air into the basin after the cleaning step has been carried out, thereby making it possible to remove water (or detergent) attached to or remaining on the outer surface of the endoscope and the inside walls of the basin. As a result, even when liquid disinfectant is subsequently supplied to the basin in order to carry out the disinfecting step, thinning and degradation of the liquid detergent can be prevented. Moreover, by using the blowing unit to blow a gas such as air into the basin following completion of the disinfecting step as well, disinfectant remaining on the outer surface of the endoscope and the inside walls of the basin can be removed and recovered, thus making it possible to prevent a successive decline in the amount of disinfectant as endoscopes are reprocessed.

Another advantage of the same aspect of the invention is that, because the blowing unit blow a gas such as air into the basin following completion of the rinsing step as well, water attached to the outside surface of the endoscope is removed, thus making it possible to prevent, for example, droplets of fluid from falling and wetting the vicinity of the endoscope reprocessor when the endoscope is removed from the basin. Moreover, preventing such undesirable effects helps minimize the need for tasks such as wiping up moisture adhering to the endoscope.

A further advantage of the same aspect of the invention is that, because the blowing unit blows gas into the basin after the discharge of liquids from the basin, reprocessing liquid attached to the inside walls of the basin and the outer surface of the endoscope can be removed, eliminating the need for time to allow such liquids to drain out, and thus making it possible to shorten the endoscope reprocessing time.

BRIEF DESCRIPTION OF THE DIAGRAMS

DETAILED DESCRIPTION OF THE INVENTION

The endoscope reprocessors according to the present invention are described in detail below based on the preferred embodiments shown in the attached diagrams.

First, the endoscope reprocessor according to the first aspect of the invention is described in conjunction with FIGS. 1 to 11B.

Figure 1:
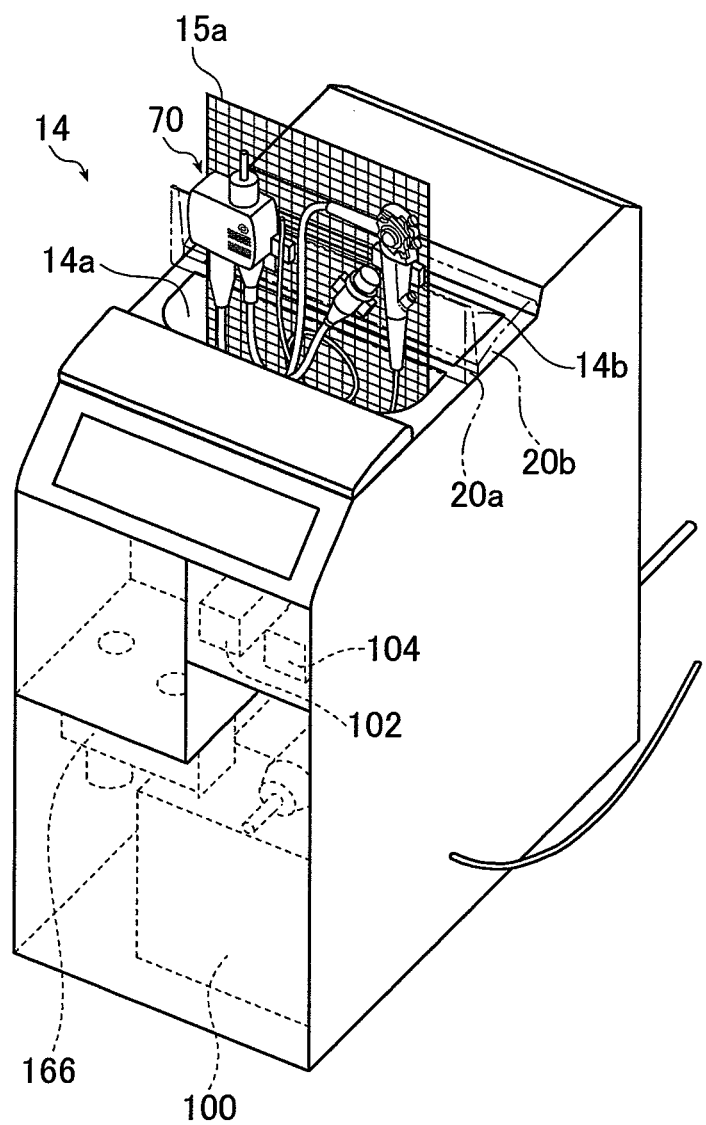
FIG. 1 is a schematic, perspective view showing an endoscope reprocessor in accordance with one embodiment of the first aspect of the present invention.
Figure 2:
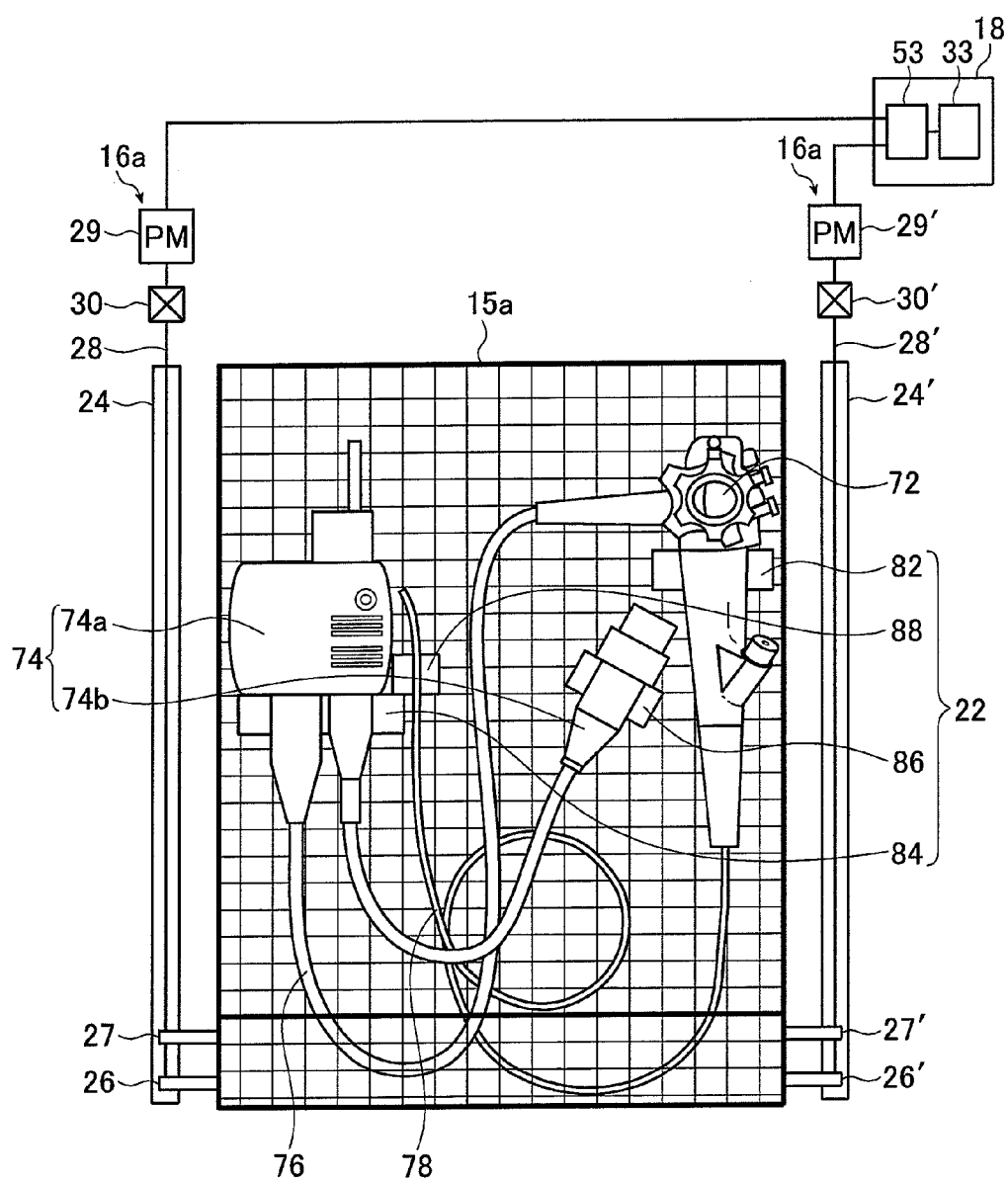
FIG. 2 is a front view illustrating schematically the rack (with an endoscope mounted thereon) and the drive mechanism of the endoscope reprocessor shown in FIG. 1.
Figure 3:
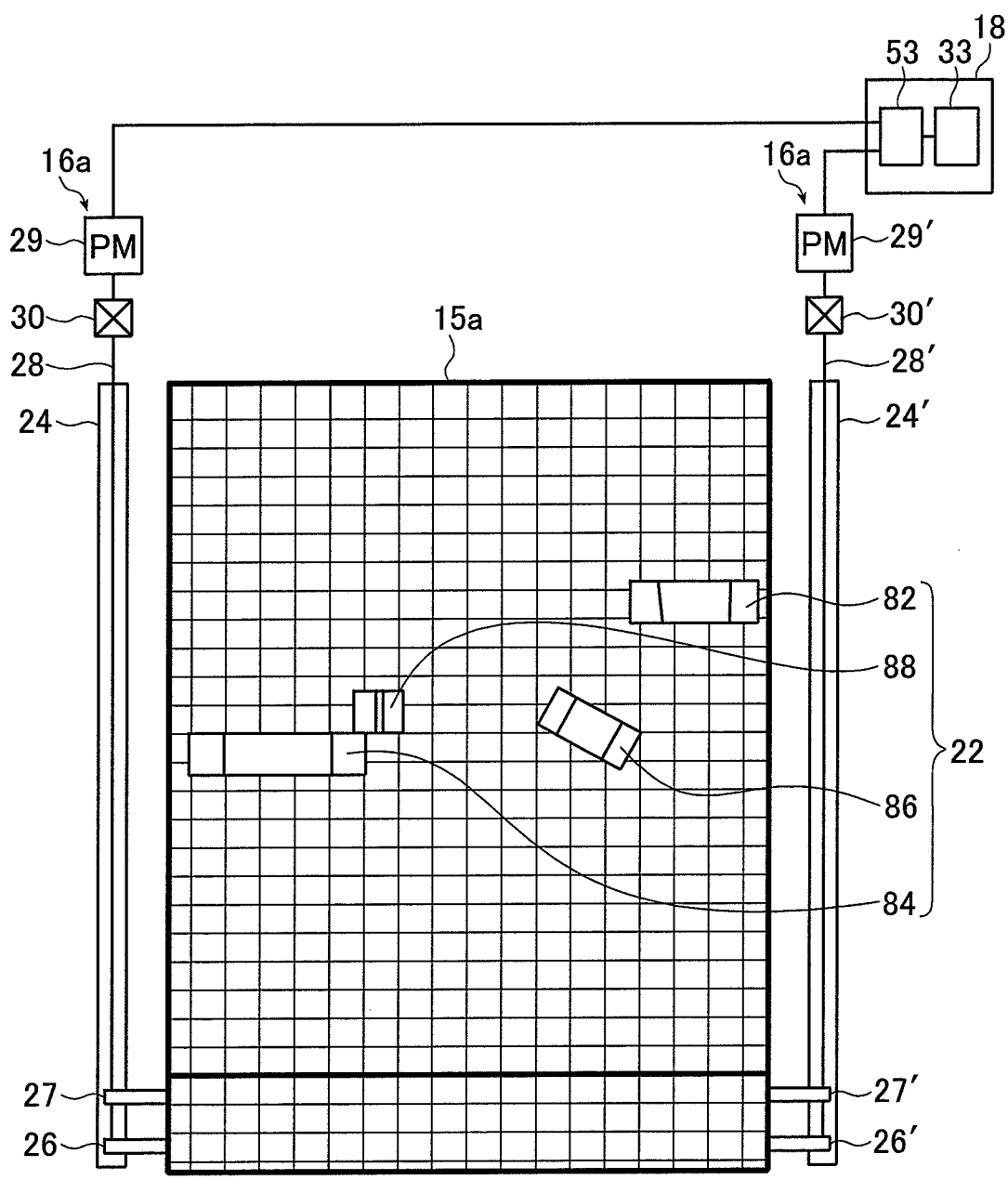
FIG. 3 is a front view illustrating schematically the rack (with the endoscope removed) and the drive mechanism of the endoscope reprocessor shown in FIG. 2.
Figure 4:
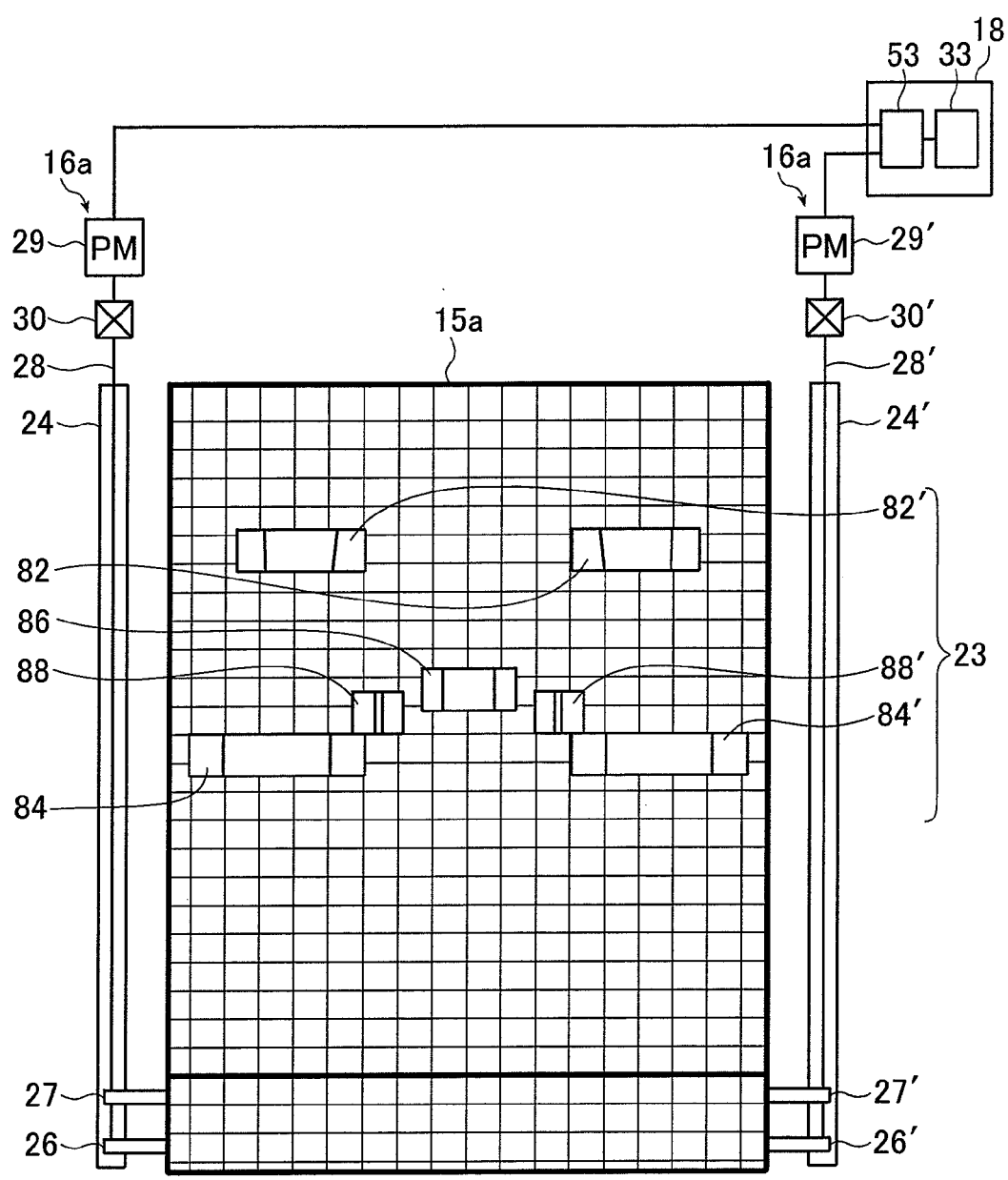
FIG. 4 is a front view illustrating schematically another example of a rack and a drive mechanism such as may be used in the endoscope reprocessor shown in FIG. 1.
Figure 5:
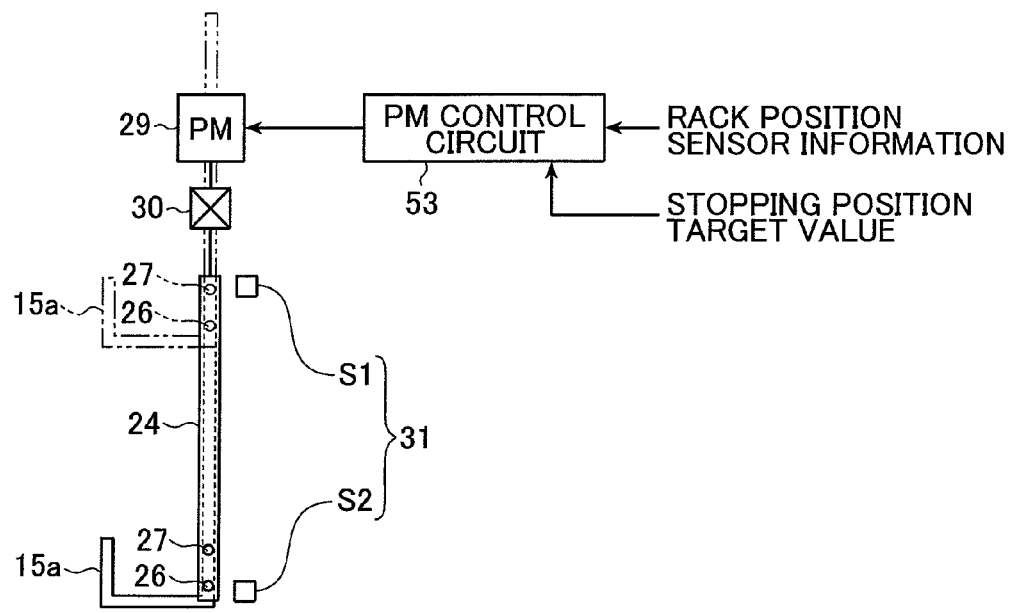
FIG. 5 is a side view illustrating schematically the rack and the drive mechanism shown in FIG. 3.
Figure 6A:
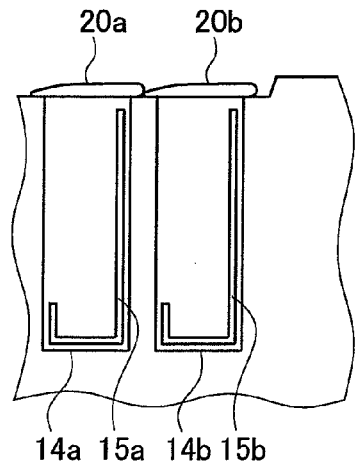
FIGS. 6A and 6B are partial cross-sectional views, each illustrating schematically the basin and the rack of the endoscope reprocessor shown in FIG. 1 in different states of use.
Figure 6B:
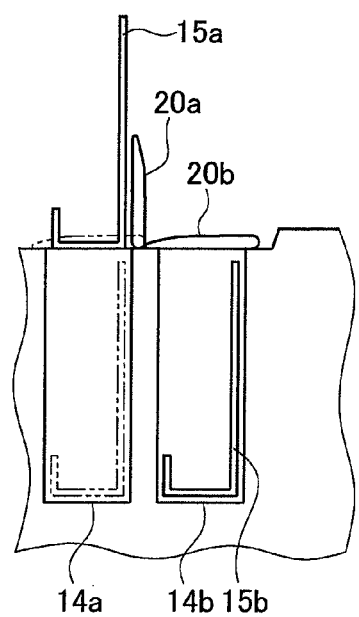

FIG. 1 is a perspective view illustrating schematically an endoscope reprocessor 10 according to one embodiment of the endoscope reprocessor of the first aspect of the invention. FIGS. 2 and 3 are front views showing schematically a rack 15a and a drive mechanism 16a of the endoscope reprocessor 10 shown in FIG. 1. FIG. 4 is a front view showing schematically another example of the rack, and FIG. 5 is a side view showing schematically the rack and the drive mechanism shown in FIG. 3. FIGS. 6A and 6B are partial cross-sectional views showing schematically a first basin 14a and second basin 14b and a first rack 15a and second rack 15b in the endoscope reprocessor 10 shown in FIG. 1. In addition, FIG. 2 shows the first rack 15a with an endoscope 70 situated thereon, and FIG. 3 shows the first rack 15a with no endoscope 70 situated thereon. In FIGS. 5, 6A and 6B, the locking unit and endoscope on the rack are omitted from the diagrams so as to more clearly illustrate the arrangement of the rack and the drive mechanism.

Referring to FIG. 1, the endoscope reprocessor (also referred to below simply as the "reprocessor") 10 has a first basin 14a and a second basin 14b (both of which are also referred to collectively below as "basin 14"), a first rack 15a and a second rack 15b which are disposed at the interior of, respectively, the first basin 14a and the second basin 14b, a first drive mechanism 16a for raising and lowering the first rack 15a, a second drive mechanism for raising and lowering the second rack 15b, a controller 18, a liquid detergent tank 100, a liquid disinfectant tank 102, an alcohol tank 104 and a filter 166. The second drive mechanism for raising and lowering the second rack 15b is not shown in the illustrated case, but the second drive mechanism has the same construction as the first drive mechanism 16a for raising and lowering the first rack 15a.

The foregoing reprocessor 10 receives an endoscope 70 in each of the first basin 14a and the second basin 14b and reprocesses the endoscopes 70 by performing an endoscope 70 cleaning and disinfecting process that entails carrying out four steps: cleaning with a liquid detergent (cleaning step), rinsing with tap water (post-cleaning rinsing step), disinfecting with a liquid disinfectant (disinfecting step), and rinsing with tap water (post-disinfecting rinsing step).

The reprocessor 10 reprocesses two endoscopes 70 independently and asynchronously in, respectively, the first basin 14a and the second basin 14b. That is, the first basin 14a and the second basin 14b are each able to independently reprocess an endoscope 70.

Two basins 14a and 14b, two racks 15a and 15b and two drive mechanisms 16a and 16b (See FIG. 8) are provided in the present embodiment. Because the first basin 14a, the first rack 15a and the first drive mechanism 16a are in all respects identical with, respectively, the second basin 14b, the second rack 15b and the second drive mechanism 16b, save for the positions at which they are disposed, descriptions given below of the first basin 14a, the first rack 15a and the first drive mechanism 16a apply as well to the second basin 14b, the second rack 15b and the second drive mechanism.

The first basin 14a and second basin 14b of the reprocessor 10 are arranged in parallel in the depth direction from the side of the unit where the operator stands and carries out work (referred to below as the "control face"). That is, the first basin 14a is positioned closer to the control face, and the second basin 14b is positioned farther away from the control side.

The first basin 14a, which is a basin for cleaning and disinfecting an endoscope 70, has a horizontal cross-section which is substantially of rectangular shape and has a vertical height which is greater than the length of the horizontal cross-section in a lengthwise direction thereof. The first basin 14a has an opening provided on the upper side in a vertical direction. In the horizontal cross-section of the first basin 14a, the lengthwise direction is parallel to the control face. That is, the first basin 14a and the second basin 14b are arranged in parallel with long sides of the respective rectangular cross-sections thereof facing frontally (toward the control face) so as to be mutually adjacent.

The first basin 14a has an opening on which is disposed a first lid 20a that can be opened and closed. No particular limitation is imposed on the method of opening and closing the first lid 20a. For example, the lid may be opened and closed manually, with a foot pedal, or with a sensor. The use of a foot pedal or sensor is preferable in that the operator is thereby able to open and close the lid while holding an endoscope.

Referring to FIGS. 2 and 3, the first rack 15a is a plate-like member which is disposed along a surface of the first basin 14a on a side thereof away from the control face of the endoscope reprocessor 10, and has an upturn on a bottom side thereof. Specifically, the first rack 15a is composed of a plate portion having a shape which runs parallel to the control face of the endoscope reprocessor 10 and is disposed along the far side of the first basin 14a from the control face, a bottom portion which is situated at the lower end of the plate in the perpendicular direction, and an upturned portion which is parallel to the plate portion and disposed on the control face side of the first basin 14a. The plate portion of the first rack 15a has provided thereon locking unit 22 for securing various portions of the endoscope 70 at a plurality of places.

Referring to FIG. 2, the plate portion, bottom portion and upturned portion of the first rack 15a are each formed of a lattice of multiple intersecting wire-like members (e.g., metal wire).

By giving the first rack 15a a lattice shape, liquid drainage can be improved and the water used for rinsing can be prevented from remaining behind, mixing with the disinfectant, and thereby diluting the disinfectant.

Moreover, by giving the first rack 15a a lattice shape, the surface area of contact between the endoscope 70 and the first rack 15a can be reduced, enabling the endoscope to be efficiently cleaned and disinfected.

The locking unit 22 is composed of a plurality of locking members 82, 84, 86 and 88, each of which is fastened to the plate portion of the first rack 15a. The locking unit 22 secures various portions of the endoscope 70 with the respective locking members 82, 84, 86 and 88, thereby securing the endoscope 70 at a predetermined position on the first rack 15a.

The endoscope 70 in the present embodiment includes a control unit 72 for controlling the scope angle, suction, and air and water supply, a connector 74 for connection to a light source and a power supply, a universal cord 76 for connecting together the control unit 72 and the connector 74, and an insertion tube 78 which is inserted into the body of the patient. The connector 74 is itself composed of a main connector 74a and a branch connector 74b.

The locking unit 22 secures the endoscope 70 to the first rack 15a by securing the control unit 72 with the first locking member 82, securing the main connector 74a with the second locking member 84, securing the branch connector 74b with the third locking member 86, and securing the insertion tube 78 with the fourth locking member 88. In addition, cord-like portions of the endoscope 70, such as the elongated insertion tube 78 and the universal cord 76 are supported by the bottom portion and the upturned portion of the first rack 15a, and thereby held on the interior of the first rack 15a.

The method for securing the endoscope 70 with the respective locking members of the locking unit 22 is not subject to any particular limitation. For example, the endoscope 70 may be secured by clamping a portion thereof to the first rack 15a, or may be secured by loading a portion thereof on the first rack 15a.

Also, the positions of the locking members are not subject to any particular limitation; the locking members may be disposed at any position on the first rack 15a.

For example, two sets of locking members for securing various portions of the endoscope 70 may be provided as the locking unit, with the respective locking members being disposed at symmetric positions.

Specifically, as shown in FIG. 4, locking unit 23 may be composed of two locking members 82 and 82' for securing the control unit 72, two locking members 84 and 84' for securing the main connector 74a, a locking member 86 for securing the branch connector 74b, and two locking members 88 and 88' for securing the insertion tube 78. In this embodiment, the locking member 86 for securing the branch connector 74b is used in common with both sets of the other locking members.

By symmetrically providing in this way locking members for securing the respective portions of the endoscope 70, the endoscope 70 can be set on the rack 15a in the same way, regardless of which hands the operator uses to hold, respectively, the control unit 72 and the main connector 74a of the endoscope 70. By symmetrically arranging the locking members in this way, the operator, whether right-handed or left-handed, is able to hold the heavier component in the dominant hand and set the endoscope 70 on the rack 15a, thus making it easy for the operator to set the endoscope 70 in place.

The endoscope 70 can thus be set on the rack 15a by securing the major portions of the endoscope 70 to predetermined positions with the locking unit. Moreover, by using the rack 15a and the locking unit to secure portions of the endoscope 70 at higher positions than the bottom of the rack 15a, the cord portions of the endoscope 70 may be suspended downward, enabling twists and kinks in the cord portions of the endoscope 70 to be easily corrected or, because the need for correction is eliminated, making it easier to set the endoscope 70 in place. In addition, twists and kinks may be corrected while securing portions of the endoscope 70 with the locking unit 23.

Also, by securing given portions of the endoscope 70 with the locking members, the endoscope 70 can be placed against the rack 15a, enabling the surface area of contact between the rack 15a and the endoscope 70 to be made constant, and also fixing the position of the endoscope 70, thus enabling the endoscope 70 to be efficiently cleaned and disinfected.

By providing the rack 15a with a bottom portion and an upturned portion, the cord portions of the endoscope 70 can be prevented from hanging down below the rack 15a, thus making it easier to set the endoscope 70 on the rack 15a and also easier to remove the endoscope 70.

The first drive mechanism 16a includes guides 24 and 24', pins 26, 26', 27 and 27', wires 28 and 28', pulse motors 29 and 29', reduction gears 30 and 30' and a rack position detector 31 (see FIG. 5), and moves the first rack 15a upward and downward.

Here, the guide 24, the pins 26 and 27, the wire 28, the pulse motor 29 and the reduction gear 30 are disposed on one side of the first rack 15a, and the guide 24', the pins 26' and 27', the wire 28', the pulse motor 29' and the reduction gear 30' are disposed opposite the foregoing members on the other side of the first rack 15a. However, apart from the particular side of the first rack 15a on which they are disposed, these members have the same construction and function. The descriptions of the guide 24, the pins 26 and 27, the wire 28, the pulse motor 29 and the reduction gear 30 situated on one side of the first rack 15a that follow apply similarly to the corresponding members situated on the other side of the first rack 15a.

The guide 24 is a rail-like member which is situated along a side of the rack 15a (extending in the vertical direction) so as to be opposed to the guide 24'.

The first pin 26 is attached at the bottom side of the plate portion of the rack 15a, and is inserted at one end into the rail of the guide 24.

The second pin 27 is situated above and separated from the first pin 26 by a given interval. Like the first pin 26, it is attached at the bottom side of the plate portion of the rack 15a, and is inserted at one end into the rail of the guide 24.

The wire 28, which is disposed along the guide 24, is connected at one end to the first pin 26 and wound at the other end onto the pulse motor 29.

The pulse motor 29 (also referred to below as simply "motor 29") is a motor which turns in both directions and is able to either take up the wire 28 or let it out. It is advantageous to use a pulse motor like that in the present embodiment for the unit of taking up or letting out the wire 28 because the degree of rotation per pulse can be fixed to regulate the amount of wire take-up by pulse control, thus enabling the rack height to be properly adjusted. However, use may instead be made of various other types of motors.

The reduction gear 30 is provided between the motor 29 and the guide 24 so as to be in contact with the wire 28. Providing a reduction gear 30 stabilizes movement of the rack 15a by the motor 29, enabling more precise adjustment of the rack 15a position.

The drive mechanism 16a functions as follows. The motor takes up the wire 28, causing the first and second pins 26 and 27 to rise upward along the guide 24, which in turn causes the rack 15a to which the pins 26 and 27 are attached to move upward. When the drive mechanism 16a rotates the motor 29 in the opposite direction, the wire 28 that has been taken up is let out, allowing the pins 26 and 27 to descend along the guide 24, and thereby causing the rack 15a to which the first pin 26 is attached to move vertically downward.

The drive mechanism 16a, by rotating the motors 29, 29' and taking up the wires 28, 28', raises the rack 15a from a position housed within the first basin 14a (see FIG. 6A) to a position where the rack 15a emerges from the first basin 14a (FIG. 6B), and conversely lowers the rack 15a, moving it from the position shown in FIG. 6B to the position shown in FIG. 6A.

In this way, the operator can, by using the drive mechanism 16a to raise and lower the rack 15a, set the endoscope 70 on the rack 15a that has emerged from the basin 14a without having to remove the rack 15a from the reprocessor 10. Because it is thus possible, without lifting up the rack 15a, to set the endoscope 70 on the rack 15a that has emerged from the basin 14a, loading the endoscope 70 in the reprocessor 10 is easy.

The rack position sensor 31 has a top dead center sensor S1 and a bottom dead center sensor S1.

The top dead center sensor S1 is situated at a top end of the guide 24 and detects whether the rack 15a is at the top dead center. The bottom dead center sensor S2 is situated at a bottom end of the guide 24 and detects whether the rack 15a is at the bottom dead center.

The method by which the top dead center sensor S1 and the bottom dead center sensor S2 detect the rack 15a is not subject to any particular limitation and may involve, for example, detecting the first and second pins 26 and 27 attached to the rack 15a, or alternatively placing a mark on the rack 15a and detecting the mark to determine whether the rack 15a is at the top dead center or the bottom dead center of the guide 24.

In the present embodiment, the rack 15a position is detected by the top dead center sensor S1 and the bottom dead center sensor S2, although the invention is not limited in this regard. Additional sensors may be disposed, enabling the position of the rack 15a to be detected with greater precision. It is also possible to detect the position of the rack 15a by detecting, for example, distances from the pins, bottom side, lower end, top end and the like to an appropriately set reference point. Alternatively, the position of the rack 15a may be computed from the amount of wire 28 that is taken up or the amount of motor rotation.

A controller 18 has a position adjustor 33 and a pulse motor control circuit 53, and controls operation of the motors 29, 29' in the drive mechanism 16a.

The position adjustor 33 computes the target stopping position of the rack 15a based on information that has been furnished.

The pulse motor control circuit 53 computes the amount of rotation by the motor 29 based on position information for the rack 15a detected by the top dead center sensor S1 and the bottom dead center sensor S2 and on a stopping position target value computed by the position adjustor 33 (i.e., the target stopping position), and controls the amount of rotation by the motor 29.

That is, in the controller 18, the position adjustor 33 computes the stopping position target value for the rack 15a, and the pulse motor control circuit 53 computes the amount of rotation by the motor 29 from the current position of the rack 15a and the stopping position target value of the rack 15a. In addition, based on the computed value, the pulse motor control circuit 53 causes the motors 29 and 29' of the drive mechanism 16a to rotate, thereby moving the rack 15a.

The controller 18 not only moves the rack 15a, it also carries out various control of the reprocessor 10. This is described in detail later in the specification. In the present embodiment, the position adjustor 33 and the pulse motor control circuit 53 are provided in the controller 18, although they may instead be provided in the drive mechanisms 16 and 16'.

By thus enabling the height of the rack 15a to be regulated by the position adjustor 33 and the pulse motor control circuit 53 of the controller 18, the position of the rack 15a at the time the work of setting the endoscope 70 on the rack 15a is carried out (referred to below as "the rack 15a stopping position") can be adjusted for the operator.

For example, when the operator is a tall individual, the rack 15a stopping position can thus be set to a position that is higher than the standard height. On the other hand, when the operator is a short individual, the rack 15a stopping position can be set to a position that is lower than the standard height. This makes it possible for the operator to set the endoscope 70 on the rack 15a at a comfortable working height, regardless of the physical stature, such as the height, of the operator.

In this way, the operator is able to easily set the endoscope 70 on the rack 15a in a short period of time without incurring greater stress or strain.

Next, the detergent tank 100 is a reservoir for holding liquid detergent used to clean the endoscope 70. In the first basin 14a and the second basin 14b, the detergent is diluted to a predetermined ratio with water and used. The detergent solution (processing liquid) that has been diluted and used for cleaning an endoscope 70 is discarded as wastewater after each cleaning operation.

The disinfectant tank 102 is a reservoir for holding liquid disinfectant. The liquid disinfectant that has been used in the reprocessor 10 can be used in several disinfecting operations. Therefore, the liquid disinfectant supplied from the disinfectant tank 102 to the first basin 14 or the second basin 14b is recovered to the disinfectant tank 102 following a disinfecting operation. After it has been used a specific number of times, the disinfectant is discarded as wastewater.

The alcohol tank 104 is a reservoir for holding alcohol to be used for alcohol flushing.

The reprocessor 10 has a single disinfectant tank 102 for the two basins 14a, 14b, meaning that the single disinfectant tank 102 is shared by both basins 14a, 14b. Moreover, because the reprocessor 10 also has one detergent tank 100 and one alcohol tank 104, each of these is likewise shared by the two basins 14a and 14b.

It is also possible for the endoscope reprocessor of the present invention to have three or more basins, in which case the number of disinfectant tanks is one or more, so long as it is less than the number of basins. For example, if the reprocessor has three basins, the number of disinfectant tanks may be set to one which is shared among the three basins, or the number of disinfectant tanks may be set to two, with one of the disinfectant tanks being shared by two of the three basins. That is, in the endoscope reprocessor of the invention, at least two of the plurality of basins share a single disinfectant tank.

Next, the plumbing in the reprocessor 10 is described.

Figure 7:
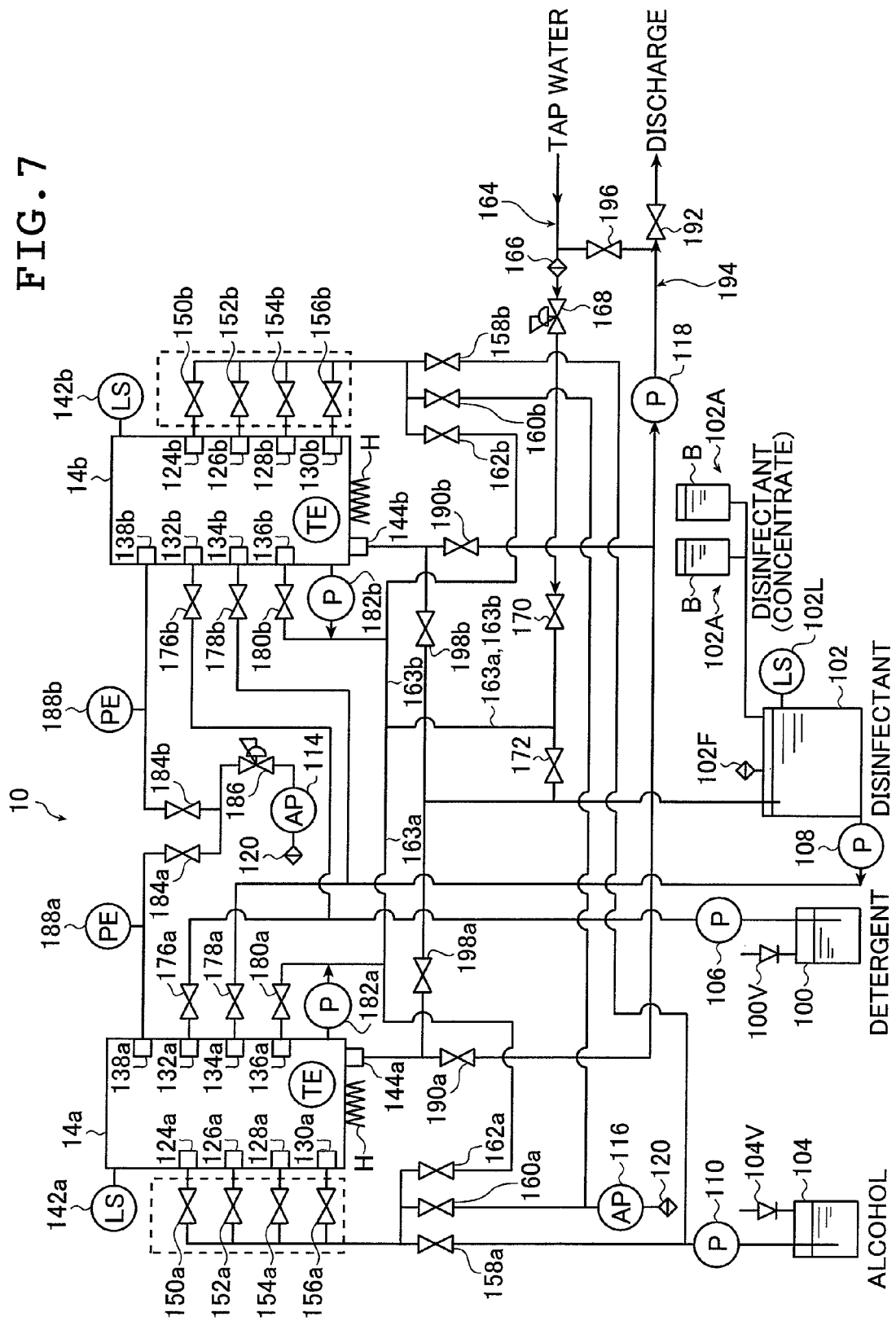
FIG. 7 is a piping diagram illustrating schematically an example of the fluid distribution lines for the endoscope reprocessor shown in FIG. 1.

FIG. 7 is a block diagram showing schematically the fluid distribution system in the reprocessor 10 shown in FIG. 1. As shown in FIG. 7, the reprocessor 10 has one detergent pump 106 which supplies liquid detergent from the detergent tank 100 to the basins 14a and 14b, one disinfectant pump 108 which supplies disinfectant from the disinfectant tank 102 to the basins 14a and 14b, and one alcohol pump 110 which supplies alcohol from the alcohol tank 104 to the basins 14a and 14b. Use of each of these pumps is shared between the two basins 14a and 14b.

Any of various known pumps may be used as these pumps, although the use of metering pumps is of course preferred. If the respective tanks are positioned lower than the basins 14a, 14b, the use of self-priming metering pumps such as diaphragm pumps is preferred.

The reprocessor 10 has one each of the following: a first air pump 114 for carrying out water leak detection on each channel of the endoscope 70, a second air pump 116 for supplying air to each channel of the endoscope 70, and a discharge pump 118 for discharging water or processing liquid within the basins 14a and 14b. Each of these is shared by the two basins 14a and 14b. Air filters 120 are provided at the air inlets of the first air pump 114 and the second air pump 116.

In the illustrated embodiment, the disinfectant tank 102 is provided with a level sensor 102L for measuring the amount of disinfectant in the tank, and mounts 102A for mounting disinfectant bottles B filled with liquid disinfectant, which mounts 102A supply liquid disinfectant to the disinfectant tank 102. In the reprocessor 10 shown in FIG. 7, two mounts 102A, 102A have been provided for the purpose of illustration. The disinfectant tank 102 also is provided with a deodorizing filter 102F for preventing the disinfectant odor from leaking to the exterior. In addition, the disinfectant tank 102 may have an air filter for preventing the entry of foreign matter such as dust and bacteria into the disinfectant tank 102.

In the reprocessor 10, the disinfectant bottles B are constructed so as to be capable of maintaining the mounted state until replenishment with fresh disinfectant. The disinfectant bottles B may serve as lids for the mounts 102A, i.e., as lids for the disinfectant tank 102.

The detergent tank 100 is equipped with a check valve 100V to prevent the unintended discharge of liquid detergent from the detergent tank 100. The alcohol tank 104 is similarly equipped with a check valve 104V to prevent the unintended discharge of alcohol from the alcohol tank 104.

Because the first basin 14a and the second basin 14b are basically of like construction and the fluid distribution systems for them are largely the same, the description of the first basin 14a that follows applies also to the second basin 14b, save for those features of the latter which differ and are separately described. Reference symbols for features of the second basin 14b are given in parentheses following reference symbols for corresponding features of the first basin 14a.

The first basin 14a (second basin 14b) is equipped at the interior with a forceps port 126a (126b) for connection to a forceps channel opening in the endoscope 70, an air/water supply port 128a (128b) for connection to an air/water supply channel opening in the endoscope 70, and a suction port 130a (130b) for connection to a suction channel opening in the endoscope 70. In addition, for endoscopes having a forceps elevator channel, a forceps elevator port 124a (124b) for connection to an opening in the forceps elevator channel is also provided.

The first basin 14a (second basin 14b) is also equipped at the interior with a detergent port 132a (132b) for introducing liquid detergent, a disinfectant port 134a (134b) for introducing liquid disinfectant, a feedwater port 136a (136b) for introducing tap water, an air port 138a (138b) for introducing air for carrying out water leak detection, and a drain port 144a (144b).

In addition, the first basin 14a is provided with a level sensor 142a (142b) for detecting the amount of liquid in the basin, a thermometer TE for measuring the liquid temperature in the basin, and a heater H for heating liquid within the basin.

An example of a suitable level sensor 142a is one which can detect the amount of liquid at four different levels. Alternatively, four level sensors may be provided.

The following are connected in common to first, second and third shared valves 158*a*, 160*a* and 162*a* (158*b*, 160*b* and 162*b*): the forceps elevator port 124*a* (124*b*) through a valve 150*a* (150*b*), the forceps port 126*a* (126*b*) through a valve 152*a* (152*b*), the air/water supply port 128*a* through a valve 154*a* (154*b*), and the suction port 130*a* through a valve 156*a* (156*b*).

The valves used in the endoscope reprocessor 10 are not subject to any particular limitation. Known valves capable of automatic opening and closing, such as solenoid valves and electrically operated valves, may be used. However, for a number of reasons, such as the small dead space within the valve, it is preferable for electrically operated valves to be used as the valves provided on the lines which discharge waste from the basins 14*a*, 14*b* or return disinfectant to the disinfectant tank.

The first shared valve 158*a* (158*b*) is connected to the alcohol supply pump 110 for the alcohol tank 104.

The second shared valve 160*a* (160*b*) is connected to the second air pump 116 for introducing air into the channels of the endoscope 70.

And the third shared valve 162*a* (162*b*) is connected to a water supply line 164 for supplying tap water to various places in the reprocessor 10.

The water supply line 164 is connected to, for example, a spigot on a water pipe, and serves to supply tap water to the reprocessor 10. As shown in FIG. 7, it has, from the upstream side, a filter 166 for preventing the entry of foreign matter, a pressure reducing valve 168 for preventing excessive force from acting on the plumbing within the reprocessor, a first valve 170, and a second valve 172.

The line from the third shared valve 162*a* (162*b*) is connected to the water supply line 164 between the first valve 170 and the second valve 172. For the sake of convenience, the line that extends from the third shared valve 162*a* (162*b*) to a point between the first valve 170 and the second valve 172 is referred to below as water supply line 163*a* (163*b*). This water supply line 163*a* (163*b*) branches at some intermediate point, connecting to a subsequently described circulation pump 182*a* (182*b*) on the first basin 14*a* (second basin 14*b*) and a valve 180*a* (180*b*) provided on the feedwater port 136*a* (136*b*).

The second valve 172 is connected to a valve 190*a* (190*b*) which is connected to the drain port 144*a* (144*b*) on the first basin 14*a* (second basin 14*b*).

The detergent port 132*a* (132*b*) is connected to the detergent pump 106 through a valve 176*a* (176*b*). The disinfectant port 134*a* (134*b*) is connected to the disinfectant pump 108 through a valve 178*a* (178*b*). This line from the disinfectant tank 102 to the disinfectant port 134*a* (134*b*) on the first basin 14*a* (14*b*), the disinfectant pump 108 and the valve 178*a* (178*b*) together constitute the disinfectant supply unit of the present invention. In addition, the feedwater port 136*a* (136*b*) is connected to the water supply line 163*a* (163*b*) through the valve 180*a* (180*b*). In other words, the branched line which branches from the water supply line 163*a* (163*b*) is connected to the valve 180*a* (180*b*); i.e., to the feedwater port 136*a* (136*b*).

A circulation pump 182*a* (182*b*) is connected to the first basin 14*a* (second basin 14*b*). This circulation pump 182*a* supplies liquid within the first basin 14*a* to a branched line which branches from the water supply line 163*a* and extends to the valve 180*a*, i.e., the feedwater port 136*a*.

An air port 138*a* (138*b*) which introduces air for water leak detection is connected through a valve 184*a* (184*b*) to a pressure reducing valve 186 connected to the first air pump 114.

A pressure gauge 188*a* (188*b*) is situated on the line from the air port 138*a* (138*b*) to the valve 184*a* (184*b*). It is preferable for the pressure gauge 188*a* (188*b*) to have a pressure transmitter which outputs signals to the first air pump 114 when the pressure has reached a predetermined value.

The drain port 144*a* (144*b*) is connected to the discharge pump 118 through a valve 190*a* (190*b*).

The discharge pump 118 delivers liquid, etc. within the basins 14*a*, 14*b* to a discharge line 194 having a valve 192. The water supply line 164 and the discharge line 194 are connected, through a bypass valve 196, between the upstream side of the filter 166 on the water supply line 164 and the upstream side of the valve 192 on the discharge line 194.

The line between the drain port 144*a* (144*b*) and the valve 190*a* (190*b*) branches at some intermediate point, connecting through a valve 198*a* (198*b*) to the second valve 172 on the water supply line 164 and to the disinfectant tank 102. This path from the drain port 144*a* (144*b*) on the first basin 14*a* (14*b*) to the disinfectant tank 102, and the valve 198*a* (198*b*) together constitute the disinfectant recovering unit of the present embodiment.

The plumbing for the reprocessor 10 is substantially as described above.

Figure 8:
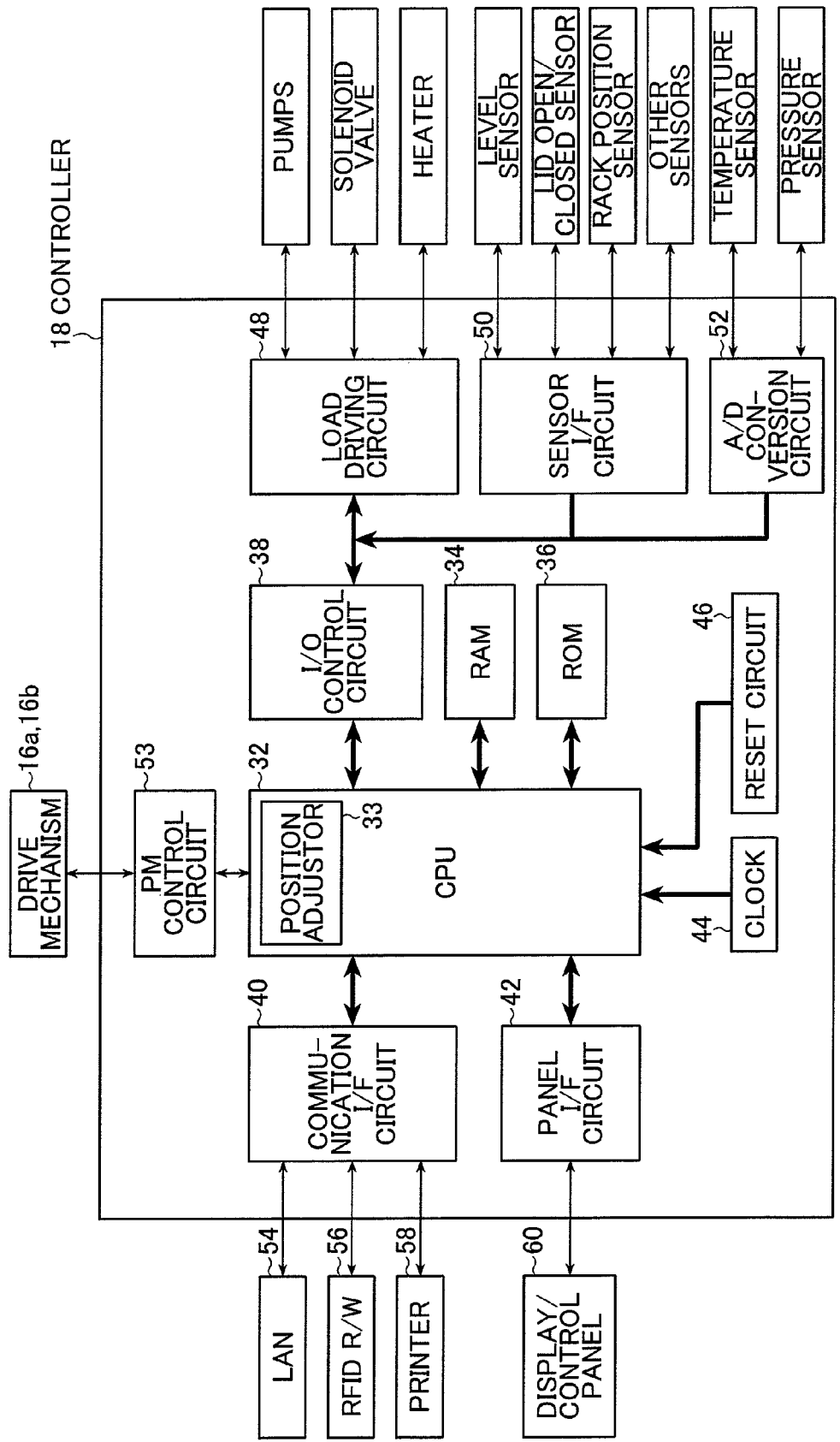
FIG. 8 is a block diagram illustrating schematically an example of the controller for the endoscope reprocessor shown in FIG. 1.

The controller 18 controls movement of the above-described first rack 15*a* and second rack 15*b* (i.e., adjusts the height of the first rack 15*a* and the second rack 15*b*), and also controls the cleaning and disinfecting steps in the first basin 14*a* and the second basin 14*b*. FIG. 8 is a block diagram which conceptually illustrates the configuration of the controller 18.

As shown in FIG. 8, the controller 18 has a CPU 32, a RAM 34, a ROM 36, an input/output (I/O) control circuit 38, a communication interface (I/F) circuit 40, a panel interface (I/F) circuit 42, a clock 44, a reset circuit 46, a load driving circuit 48, a sensor interface (I/F) circuit 50, an analog-to-digital (A/D) conversion circuit 52, and the above-mentioned pulse motor control circuit 53.

The CPU 32 controls the cleaning and disinfecting process in the endoscope reprocessor 10. A single CPU 32 carries out control for both the first basin 14*a* and the second basin 14*b*. The above-described position adjustor 33 is situated in the CPU 32 and controls the stopping positions of the first and second racks 15*a*, 15*b* based on values computed by the position adjustor 33 and on various information.

If the endoscope reprocessor 10 has three or more basins, with regard to at least the plurality of basins which share the same disinfectant tank, it is preferable for the cleaning and disinfecting process at those basins to be controlled by a single CPU 32.

The ROM 36 stores various application programs, including cleaning and disinfecting process control programs, and also stores historical data on cleaning and disinfection in the endoscope reprocessor 10, operator heights, and first and second rack 15*a*, 15*b* stopping position data for each operator. A cleaning and disinfecting process control program adapted to the number of basins in the endoscope reprocessor 10 may be stored in the ROM 36 and available for readout by the CPU 32 at any time. Alternatively, a plurality of cleaning and disinfecting process control programs for various reprocessor 10 configurations ranging from one basin to any number of basins may be stored in the ROM 36, and available for selection and readout by the CPU 32 of a particular program suitable for the actual configuration of the reprocessor 10 in use.

It is also possible to furnish program variations, such as the ability/lack of ability to select various endoscope cleaning and disinfecting steps depending on the degree of soiling, store such program variations in the ROM 36 and, on instructions from the operator or selection by the CPU 32 according to the device configuration, have the CPU 32 select and read out the appropriate program.

The load driving circuit 48 is a drive circuit for the pumps (e.g., 106, 108 and 110), solenoid valves (e.g., 150*a*, 152*a*, 154*a*, 156*a* and 198*a*) and heater (H) shown in FIG. 7.

The sensor interface circuit 50 is an interface for level sensors which detect the water level in the tanks and basins (102L, 142*a*, 142*b*), sensors which detect the opening and closing of the lids on the basins 14*a*, 14*b*, and other sensors provided in the endoscope reprocessor 10.

The A/D conversion circuit 52 digitizes analog output values from temperature sensors (TE) and pressure sensors (PE).

The pulse motor control circuit 53, as mentioned above, controls the rotation and driving of the pulse motors 29, 29' based on information transmitted from the position adjustor 33 in the CPU 32 and elsewhere.

The communication interface circuit 40 serves as a circuit for communication interface with a LAN connector 54, an RFID read/write unit 56 and a printer 58 which are provided on the endoscope reprocessor 10.

The reprocessor 10 connects the controller 18 to, for example, an internal hospital network by unit of the LAN connector 54, enabling the communication of historical data on cleaning and disinfection in the reprocessor 10.

The RFID read/write unit 56 uses a radio frequency identification system (RFID) to carry out the reading and writing of information on cleaning and disinfection. For example, with the RFID read/write unit 56, reprocessing history data for an endoscope 70 can be read off an IC tag attached to the endoscope and, following cleaning and disinfection within the endoscope reprocessor 10, data for the cleaning and disinfecting process just completed can be written onto the IC tag of the endoscope 70.

Figure 9:
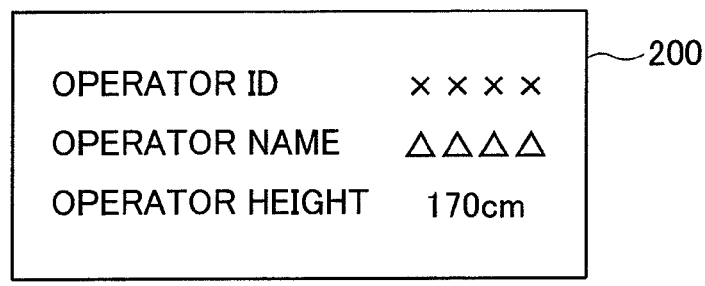
FIG. 9 is a diagram showing an example of RFID data.

Here, FIG. 9 is an explanatory diagram showing an example of IC tag information. Referring to FIG. 9, the operator ID, the name of the operator and the height of the operator are shown as examples of information read from the IC tag 200 by the RFID read/write unit 56.

In addition, information may be read from an IC tag onto which identifying information on the operator in charge of reprocessing of the endoscope 70 has been input, and the reprocessing history carried out by the operator may be written to that operator's IC tag. The CPU 32 can take various data read from an IC tag by the RFID read/write unit 56 and store it in the ROM 36 as reprocessing history data, or can send it to a network via the LAN connector 54.

Historical control data can be printed from the printer 58. This printer 58 may be mounted on the endoscope reprocessor 10, or may be an external printer.

The panel interface circuit 42 is an interface with the display/control panel 60 of the endoscope reprocessor 10. The display/control panel 60 displays information concerning the reprocessor 10, and also functions as a touch panel that allows the operator to enter instructions.

The endoscope reprocessor 10 is basically configured as described above.

In the reprocessor 10, by using the drive mechanisms to raise and lower the racks and by using a position adjustor to adjust the rack height, the stopping positions of the racks can be set to any desired height.

In this way, the racks can be adjusted to a height for each operator at which the endoscope is easy to set on the rack, enabling the endoscope to be easily set on the rack regardless of the particular operator doing the work.

By giving the basins an elongated shape in the vertical direction and providing the racks for the endoscopes in such a way that the endoscope cords are disposed along the vertical direction inside the reprocessor, the reprocessor can be given a smaller footprint and the device can be made more compact. By providing the reprocessor with a horizontal cross-section that is rectangular, even when the endoscope is vertically disposed within the reprocessor, the capacity of the reprocessor can be reduced, enabling the volume of processing liquids such as detergent and disinfectant used to clean and disinfect the endoscope to be reduced.

By setting the endoscope on a rack that is raised by a drive mechanism, there is no need for the operator to bend over when setting the endoscope in the basin, thus making it easier to load the endoscope in the reprocessor.

Moreover, by providing a plurality of basins, a plurality of endoscopes (in the present embodiment, two endoscopes) can be independently cleaned.

In addition, the apparatus can be made more compact by giving the basins a vertically elongated shape and arranging the two basins in parallel from the control face—that is, by arranging the basins so that the long sides of their horizontal cross-sections are mutually adjacent.

Also, by arranging the two basins in the manner of the present embodiment and by additionally providing drive mechanisms and using the drive mechanisms to raise the racks to a rack stopping position, an endoscope can easily be loaded even into the basin located furthest from the control face of the reprocessor.

In this way, the reprocessor can be made compact and endoscopes can be easily loaded therein.

The position adjustor 33 preferably sets the rack stopping position based on operator information read by the RFID read-write unit.

This may be done by writing information about the optimal rack stopping position onto the operator's IC tag or the like, then later reading out this information and setting the rack stopping position. Alternatively, the height and optimal rack stopping position may be stored in the ROM 36, the height data read from the operator's IC tag, and the rack stopping position set based on the height data that has been read off and a correspondence relation stored in the ROM 36. Another possibility for setting the rack stopping position is to store the previous rack stopping position for an operator in the ROM 36, read the identification number from the operator's IC tag and, based on the identification number that has been read, retrieve the corresponding rack stopping position from the ROM 36.

In this way, by setting the stopping positions for the racks 15*a* and 15*b* based on operator information, it is possible to facilitate loading of the endoscopes on the racks.

It is preferable that the position adjustor 33 separately set the stopping position for each rack. By setting the stopping position separately for each rack, even when the distances from the control face differ and the heights at which the endoscope can be easily loaded onto the racks differ, suitable rack stopping positions can be set for each rack, enabling the operator to easily load the endoscope onto the rack regardless of the position of the rack in the depth direction of the apparatus.

The RFID read/write unit preferably communicates wirelessly with the target of the read and/or write operation such as an IC tag.

In this way, the operator information can be read merely by holding up the IC tag or the like, or merely by approaching the apparatus.

In the present embodiment, the control unit, connector and insertion tube of the endoscope are secured by the locking members serving as the locking unit on the rack. However, the invention is not limited in this respect, and may instead be configured with locking members for securing only the control unit and the connector. Alternatively, a locking member for securing the universal cord may be provided, or a plurality of locking members may be provided for each component member of the endoscope.

Also, the shape of the rack is not subject to any particular limitation, provided the rack can be moved up and down by a drive mechanism and a portion of the endoscope can be secured to the rack. For example, the locking unit may be attached to the bottom portion of the rack. In such a case, by having the locking members of the locking unit be rod-like members one end of which is secured to the bottom portion of the rack and the other end of which is provided with a member such as for gripping the endoscope, all portions of the endoscope can be secured at positions of given heights from the bottom portion of the rack. Moreover, in cases where the locking unit is attached to the bottom portion of the rack, it is not absolutely essential for the rack to have a plate portion.

The drive mechanism, provided it can raise and lower the rack, is not subject to any particular limitation with regard to the driving method. For example, use can be made of various drive mechanisms, such as a linear drive, a spring drive or a chain drive. In the present embodiment, the drive mechanism is provided at the interior of the basin; however, the drive mechanism may instead be provided outside of the basin.

In the above-described embodiment, the drive mechanism moves the rack only in the vertical direction. However, the invention is not limited in this regard. For example, it is also possible to tilt the rack at a specific angle.

Figure 10:
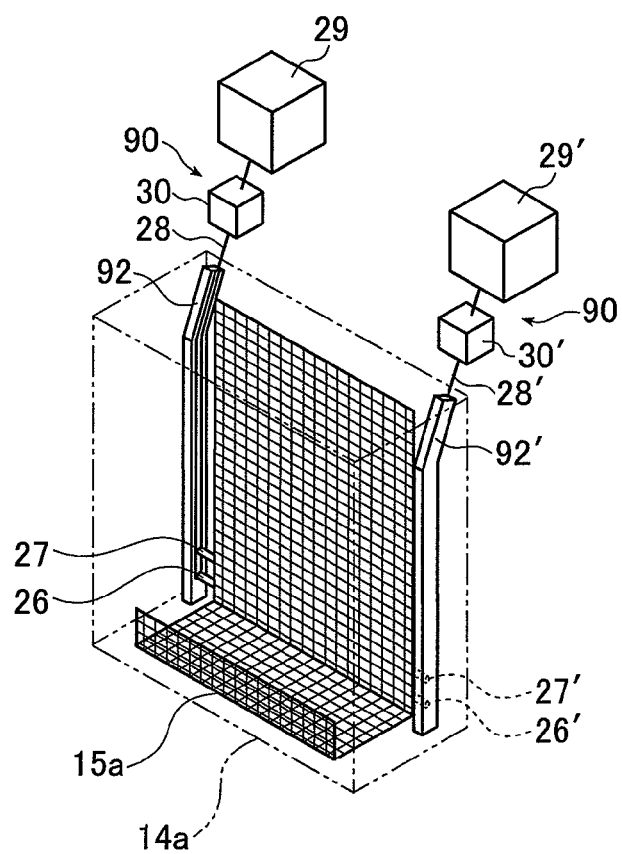
FIG. 10 is a perspective view illustrating schematically another example of a drive mechanism such as may be used in the endoscope reprocessor according to the first aspect of the invention.
Figure 11A:
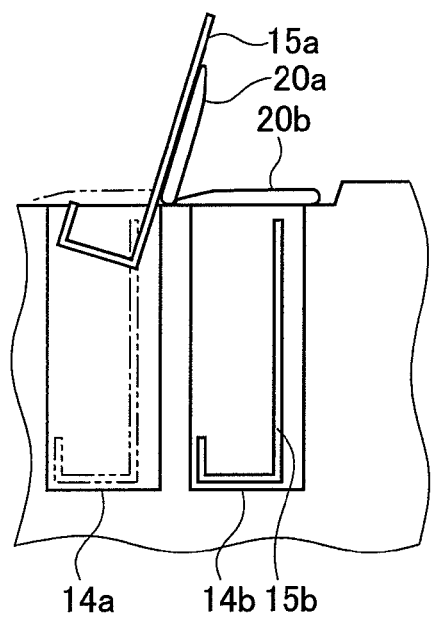
FIGS. 11A and 11B are partial cross-sectional diagrams illustrating schematically examples of the basin and the rack of the endoscope reprocessor shown in FIG. 10.
Figure 11B:
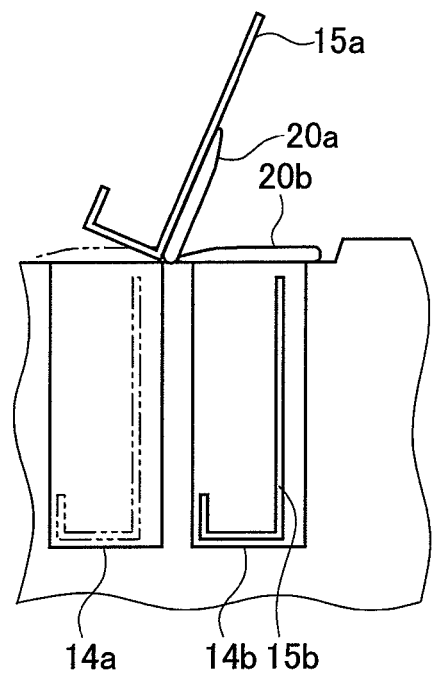

FIG. 10 is a perspective view showing schematically an example of a drive mechanism which tilts the rack. FIGS. 11A and 11B are partial cross-sectional diagrams showing examples of a rack at respective rack stopping positions. In FIG. 10 and FIGS. 11A and 11B, to more clearly illustrate the construction of the rack and the drive mechanism, the rack locking unit and the endoscope are omitted from the diagrams.

Here, aside from the shape of guides 92, 92', the drive mechanism 90 shown in FIG. 10 has the same construction as the drive mechanism 16a shown in FIGS. 2 to 4. Accordingly, distinctive features of the drive mechanism 90 are described below while denoting like elements by the same reference symbols used in connection with the earlier embodiment and omitting explanations of such like elements.

As shown in FIG. 10, the drive mechanism 90 includes the guides 92, 92', pins 26, 26', 27 and 27', wires 28, 28', and motors 29, 29'.

In this embodiment as well, because the guide 92 and other elements on one side are in all respects identical, save for the side on which they are disposed, with the guide 92' and other elements on the other side, descriptions given below of the guide 92 and other elements on one side apply equally to the guide 92' and other elements on the other side.

The guide 92 is a rail-like member which extends from a bottom side to an open side of the basin along a side wall of the rack so as to be opposed to the guide 92', with a large portion thereof from the bottom side extending in a vertical direction and a small portion thereof at the open side inclined at a specific angle toward a side of the apparatus away from the control face. That is, the guide 92 is composed of a rail which extends vertically at the bottom side of the basin, and a rail which is inclined away from the vertical direction and away from the control face at the open side of the basin.

The drive mechanism 90 also drives the motor 29 (and 29'), thereby taking up the wire 28 (and 28'), which raises the first pin 26 and the second pin 27 (and 26', 27'), and thereby raises the rack 15a which is coupled to the pins 26, 27 (and 26', 27'). In this embodiment, because the guides 92 and 92' are shaped such that a portion of each on the open side of the basin 14a is inclined at a specific angle, when the second pin 27 rises to the inclined portion of the guide 92, as shown in FIG. 11A, the rack 15a assumes a state in which it is tilted at a specific angle in a direction such that the side thereof to which the endoscope 70 is to be secured faces up.

Moreover, as the angle of inclination gradually increases and both the second pin 27 and the first pin 26 rise to the inclined portion of the guide 92, as shown in FIG. 11B, the rack 15a assumes a state in which it is tilted at a larger angle than when only the second pin 27 has risen to the inclined portion (FIG. 11A).

By thus tilting the rack, at the rack stopping position, to a specific angle in a direction where the side of the plate portion thereof on which the endoscope is to be set faces up, the operator can more easily set the endoscope on the rack.

In the present embodiment, a portion of the guide is inclined, thereby enabling the rack to be tilted at a specific angle at the rack stopping position. However, the invention is not limited in this regard. For example, at the rack stopping position, the rack can be made to pivot about one of the pins, or a plurality of guides inclined at different angles may be provided in such a way as to enable the rack angle of inclination to be adjusted by changing the guides through which the pins pass. Alternatively, a drive portion which moves the guides up and down may additionally be provided so as to adjust the height of the guides.

It is preferable here for the drive mechanism to be a mechanism which is capable of adjusting the rack angle of inclination separately from the rack height.

The ability to adjust the rack height and the rack angle of inclination independent of each other enables a height and angle of inclination at which endoscope loading is easy to be set for each operator as the rack stopping position. In this way, the operator can more easily set the endoscope on the rack.

Next, an example of an endoscope 70 cleaning and disinfecting process (reprocessing) carried out using the endoscope reprocessor 10 is described. The following description relates to the first basin 14a, although endoscope reprocessing may be carried out in exactly the same way for the second basin 14b as well. It should be noted that, in the description given below of the individual operations carried out in each step of the endoscope cleaning and disinfecting process, aside from those valves which are specifically mentioned as being open, all other valves are closed. Similarly, aside from those pumps which are mentioned as being activated, all other pumps are at rest.

First, the lid 20a is opened and the rack 15a is raised by the drive mechanism 16a up to the rack 15a stopping position.

Next, the operator mounts the endoscope 70 on the rack 15a by securing the control unit 72 with the locking member 82, securing the main connector 74a of the connector 74 with the locking member 84, securing the branch connector 74b of the connector 74 with the locking member 86, and securing the insertion tube 78 with the locking member 88. In addition, the operator connects the forceps elevator channel of the endoscope 70 to the forceps elevator port 124a, the forceps channel to the forceps port 126a, the air/water supply channel to the air/water supply port 128a, and the suction channel to the suction port 130a.

Connection between the respective ports and the respective channels of the endoscope 70 may be carried out by a known unit which involves the use of, e.g., connectors or connecting tubes and is employed in endoscope reprocessors.

When mounting of the endoscope 70 on the rack 15a is completed, the rack 15a is lowered by the drive mechanism 16a and set inside the basin 14a.

Next, after an instruction to start the cleaning and disinfecting process has been input, the reprocessor 10 begins by carrying out a cleaning step.

First, the pressure reducing valve 168 and the first valve 170 on the water supply line 164 and the valve 180a connected to the feedwater port 136a are opened, thereby introducing a specific amount of tap water from the water supply line 164, through the water supply line 163a, and into the first basin 14a via the feedwater port 136a (tap water introduction).

Once the specific amount of tap water has been introduced, the valve 176a connected to the detergent port 132a is opened, the detergent pump 106 is activated, and liquid detergent is supplied from the detergent tank 100 to the detergent port 132a, thereby introducing a given amount of liquid detergent into the first basin 14a (detergent introduction).

In the reprocessor 10, following tap water introduction in the cleaning step (between tap water introduction and detergent introduction), the subsequently described water leak detecting step may be carried out if necessary.

Alternatively, if a water leak detecting step is not carried out, tap water introduction and detergent introduction may be carried out in parallel.

After given amounts of tap water and liquid detergent have been introduced into the first basin 14a, the valve 162a is opened, the circulation pump 182a is activated and, to give one example, the valve 150a connected to the forceps elevator port 124a, the valve 152a connected to the forceps port 126a, the valve 154a connected to the air/water supply port 128a and the valve 156a connected to the suction port 130a are opened one at a time in this order for predetermined lengths of time. The valve open times may be the same or different for each port.

In this way, the detergent solution within the first basin 14a circulates through each channel of the endoscope 70, thereby carrying out, in order, the cleaning of the respective channels of the endoscope 70 with the detergent solution (channel cleaning).

Once channel cleaning has been completed, the valve 180a corresponding to the feedwater port 136a is opened, and the circulation pump 182 is activated.

This causes the detergent solution within the first basin 14a to circulate outside of the endoscope 70, thereby cleaning the exterior of the endoscope 70 with the detergent solution (exterior flow cleaning).

Once exterior flow cleaning has been carried out for a predetermined length of time, the valve 190a and the valve 192 are opened, and the discharge pump 118 is activated, thereby discharging the detergent solution within the basin 14 (detergent solution discharge).

After all the detergent solution inside the basin 14 has been discharged, leaving the valve 190a and valve 192 open, the valve 160a is also opened and the second air pump 116 is activated. In addition, the valve 150a connected to the forceps elevator port 124a, the valve 152a connected to the forceps port 126a, the valve 154a connected to the air/water supply port 128a, and the valve 156a connected to the suction port 130a are each opened one at a time in this order.

In this way, air is supplied to the respective channels of the endoscope 70 from the forceps elevator port 124a, the forceps port 126a, the air/water supply port 128a and the suction port 130a, thereby discharging from the endoscope 70 any detergent solution remaining within the channels (cleaning air supply).

The cleaning step is completed as described above, following which a post-cleaning rinsing step is carried out.

Aside from not introducing liquid detergent into the basin 14a, the post-clean rinsing step is basically carried out in the same way as the cleaning step described above.

That is, first, the pressure reducing valve 168, the first valve 170 and the valve 180a are opened, and a predetermined amount of tap water is introduced into the first basin 14a (tap water introduction).

Once a predetermined amount of tap water has been introduced into the first basin 14a, the valve 162a is opened, the circulation pump 182a is activated, and the valves 150a, 152a, 154a and 156a are each opened one at a time in this order, thereby carrying out channel rinsing in which each channel of the endoscope 70 is rinsed with tap water in the same way as in channel cleaning. Next, the valve 180a is opened and the circulation pump 182a is activated, thereby carrying out exterior flow rinsing in which the exterior of the endoscope 70 is rinsed with tap water in the same way as in exterior flow cleaning.

When exterior flow rinsing is completed, the valves 190a and 192 are opened, the discharge pump 118 is activated, and discharge is carried out in the rinsing step in the same way as in detergent solution discharge. Next, the valve 160a is opened, the second air pump 116 is activated, and the valves 150a, 152a, 154a and 156a are opened one at a time in this order, thereby carrying out air supply in the rinsing step in the same way as in cleaning air supply, thereby completing the post-cleaning rinsing step.

When the post-cleaning rinsing step has been completed, a disinfecting step is carried out.

In the disinfecting step, first the valve 178a connected to the disinfectant port 134a is opened, the disinfectant pump 108 is activated, and a predetermined amount of liquid disinfectant is introduced into the first basin 14a (disinfectant introduction).

After a predetermined amount of disinfectant has been introduced into the first basin 14a, the interior of each channel of the endoscope 70 is disinfected in the same way as in the above-described channel cleaning operation.

That is, the valve 162a is opened and the circulation pump 182a is activated, and the valves 150a, 152a, 154a and 156a connected to the ports connected to the respective channels of the endoscope 70 are opened one at a time in this order for predetermined lengths of time.

In this way, the liquid disinfectant within the first basin 14a is circulated through the respective channels within the endoscope 70, thereby disinfecting the respective channels of the endoscope 70 with the liquid disinfectant (channel disinfection).

Once channel disinfection has been completed, the exterior of the endoscope 70 is disinfected in the same way as in the above-described exterior flow cleaning operation.

That is, the valve 180a corresponding to the feedwater port 136a is opened and the circulation pump 182a is activated so as to circulate the liquid disinfectant in the first basin 14a over the exterior of the endoscope 70 and thereby disinfect the exterior of the endoscope 70 with the liquid disinfectant (exterior flow disinfection).

Once exterior flow disinfection has been carried out for a predetermined length of time, the valve 198a connected to the drain port 144a is opened, and the disinfectant is returned to the disinfectant tank 102 (disinfectant recovery).

In the endoscope reprocessor 10 shown in the diagrams, the disinfectant is not recovered using pumps and the like. Instead, the disinfectant is recovered in the disinfectant tank 102 by gravity drainage.

Once the disinfectant inside the basin 14*a* has been recovered to the disinfectant tank 102, air supply is carried out to each channel of the endoscope 70 in the same way as in the above cleaning air supply operation.

That is, the valve 160*a* is opened and the second air pump 116 is activated, and the valves 150*a*, 152*a*, 154*a* and 156*a* are opened one at a time in order. This causes air to be supplied from the forceps elevator port 124*a*, the forceps port 126*a*, the air/water supply port 128*a* and the suction port 130*a* to the respective channels of the endoscope 70, thereby causing disinfectant remaining within the channels to be discharged from the endoscope 70 (disinfection air supply).

Following completion of the disinfecting step as described above, a post-disinfection rinsing step is carried out.

The post-disinfection rinsing step is also carried out in basically the same way as the above-described post-cleaning rinsing step.

That is, first, the pressure-reducing valve 168, the valve 180*a*, and the first valve 170 are opened, and a predetermined amount of tap water is introduced into the first basin 14*a* (tap water introduction).

Once tap water introduction is completed, the valve 162*a* is opened and the circulation pump 182*a* is activated, and the valves 150*a*, 152*a*, 154*a* and 156*a* are opened one at a time in this order and for exactly a predetermined length of time, thereby carrying out channel rinsing in which each of the channels in the endoscope 70 is rinsed with tap water. Next, the valve 180*a* is opened and the circulating pump 182*a* is activated, thereby carrying out exterior flow rinsing in which the exterior of the endoscope 70 is rinsed with running water.

Once exterior flow rinsing is completed, the valves 190*a* and valve 192 are opened, the discharge pump 118 is activated, and discharge in the rinsing step is carried out. Next, the valve 160*a* is opened and the second air pump 116 is activated, and the valves 150*a*, 152*a*, 154*a* and 156*a* are opened one at a time in this order to carry out air supply in the rinsing step, thereby completing the rinsing step following the disinfecting step.

The completion of this rinsing step following the disinfecting step marks the completion of the cleaning and disinfecting process, bringing the reprocessing of the endoscope 70 to an end. The operator is alerted that reprocessing of the endoscope 70 is completed by a screen display, the generation of an audible signal or some other unit.

As described above, the endoscope reprocessor 10 shares numerous elements such as tanks and pumps between the first basin 14*a* and the second basin 14*b*. However, because each of the two basins, aside from the feed lines for liquid detergent, etc., water supply line 164 and discharge line 194, has independent plumbing, it is possible for the two basins to carry out the same processing at the same time or to carry out mutually different processing (asynchronous processing in the two basins) at the same time.

The reprocessor 10 basically carries out the endoscope 70 cleaning and disinfecting process in the manner described above. However, it is also possible for the reprocessor 10 to carry out various treatments in addition to such cleaning and disinfection.

For example, if necessary, alcohol flushing so as to accelerate drying within each channel of the endoscope 70 after cleaning and disinfection may be carried out.

When alcohol flushing is carried out, following completion of the cleaning and disinfecting process, the valve 158*a* is opened and the alcohol pump 110 is activated, and the valve 150*a* which connects to the forceps elevator port 124*a*, the valve 152*a* which connects to the forceps port 126*a*, the valve 154*a* which connects to the air/water supply port 128*a*, and the valve 156*a* which connects to the suction port 130*a* are opened one at a time in this order for predetermined lengths of time.

Next, in the same manner as in air supply in the various above-described steps, the valve 160*a* is opened and the second air pump 116 is activated, and the valves 150*a*, 152*a*, 154*a* and 156*a* are opened one at a time in this order, thereby supplying air to each channel of the endoscope 70, discharging the alcohol, and drying the channels.

The drain port 144*a* and the valves 190*a* and 192 are then opened and the discharge pump 118 is activated, thereby discharging from the system the alcohol that was discharged from the endoscope 70 channels into the first basin 14*a*.

The endoscope reprocessor 10 can also carry out a self-disinfecting step in which the water supply line 164, the discharge line 194, etc. are disinfected with disinfectant.

In this self-disinfecting step, first, the valve 178*a* connected to the disinfectant port 134*a* is opened, the disinfectant pump 108 is activated, and a predetermined amount of liquid disinfectant is introduced into the first basin 14*a*.

Next, the valve 190*a* connected to the drain port 144*a*, the bypass valve 196, the pressure reducing valve 168, the first valve 170, and the valve 180*a* connected to the feedwater port 136*a* are opened, the discharge pump 118 is activated, and the disinfectant is circulated through a path which includes the water supply line 164 and the discharge line 194.

In a preferred embodiment of the endoscope reprocessor 10 shown in the diagrams, following the completion of self-disinfection, the disinfectant within the apparatus is discharged and the disinfectant tank 102 is filled with fresh disinfectant.

That is, the liquid disinfectant is circulated for a predetermined length of time in the above-described path which includes the water supply line 164 and the discharge line 194, after which the valves 190*a* and 192 are opened and the discharge pump 118 is activated, thereby discharging the disinfectant. In addition, the valve 178*a* is opened and the disinfectant pump 108 is activated, thereby pouring all of the disinfectant remaining in the disinfectant tank 102 into the first basin 14*a* and subsequently discharging it from the reprocessor 10.

Once all of the disinfectant in the reprocessor 10 has been discharged, the pressure reducing valve 168, the first valve 170 and the second valve 172 are opened, and a predetermined amount of tap water is poured into the disinfectant tank 102. The operator then places disinfectant bottles B on the two mounts 102A. The disinfectant is, for example, gravity fed to the disinfectant tank 102, thereby filling the disinfectant tank 102 with fresh liquid disinfectant.

Moreover, as mentioned above, in the endoscope reprocessor 10, if necessary, water leak detection to detect damage and perforations in the respective channels of the endoscope 70 may be carried out following the introduction of tap water in the cleaning step.

In cases where a water leak detecting step is carried out, when the endoscope 70 to be reprocessed is set in the basin 14*a*, the air port 138*a* (138*b*) is connected to a pressurizing port for water leak detection provided in the endoscope 70. Once tap water introduction in the cleaning step is completed, the first air pump 114 is activated and the pressure reducing valve 186 and the valve 184*a* are both opened. When the reading on the pressure gauge 188*a* reaches a given pressure, the first air pump 114 is shut down. This shutdown is preferably carried out automatically in response to signals from the pressure gauge 188a to the first air pump 114 that correspond to the pressure readings.

When pressurization is completed, the operator checks visually whether any bubbles are emerging from the endoscope 70. If bubbles are evident, because one of the channels of the endoscope 70 may be leaking, reprocessing of the endoscope 70 is stopped at this time. Or, if the pressure measured by the pressure gauge 188a falls below a given value within a predetermined length of time, because one of the channels of the endoscope 70 may be leaking, reprocessing of the endoscope 70 is stopped at this time. Alternatively, a warning to the effect that one of the channels of the endoscope 70 is leaking may be generated when the pressure measured by the pressure gauge 188a falls below a given value.

An endoscope reprocessor according to the first aspect of the invention has been described in detail above. However, the first aspect of the invention is not limited to the foregoing embodiment, and may be variously modified and altered without departing from the scope and spirit of the invention.

For example, two basins are provided in the above embodiment. However, the invention is not limited in this respect, it being possible to set the number of basins to three or more or, conversely, to merely one.

Also, while it is desirable, for making the control face of the apparatus smaller, to arrange a plurality of basins in a row from the front to the back of the apparatus so that the long sides of the horizontal cross-sections thereof face one another, i.e., to arrange a plurality of basins, each having a horizontal cross-section which is rectangular, in parallel with long sides of the respective rectangular cross-sections thereof facing frontally so as to be mutually adjacent, it is also possible to arrange a plurality of basins in parallel in the width direction of the control face, i.e., to arrange a plurality of basins in a lateral row such that the short sides of the respective rectangular horizontal cross-sections thereof are mutually opposed and lie adjacent to each other.

By adopting the latter arrangement, an endoscope reprocessor equipped with the desired number of basins can be installed in a place whether there is little front-to-back space, but sufficient space in the width direction. Moreover, because the distance from the control face is the same for all the basins, the endoscopes can all be loaded onto the racks at the same rack height.

In the present embodiment, to give the reprocessor a smaller footprint and facilitate loading of the endoscopes onto the racks, the basins have been given a shape with a horizontal cross-section that is rectangular and a height in the vertical direction which is greater than the length of the basin in the longest direction of the horizontal cross-section thereof. However, the invention is not limited in this respect. For example, the basins may have a shape with a horizontal cross-section that is square or pentagonal. The basins may even be given a stepped shape.

Here, it is preferable for the basins to be given a shape such that the vertical height is greater than the length of the horizontal cross-section in the longest direction thereof. By adopting such a shape, an endoscope can be disposed within the basin in a manner so as to hang down in the vertical direction.

Moreover, in the present embodiment, the rack is tilted at a predetermined angle only when the endoscope is being set thereon. However, the invention is not limited in this respect. For example, it is possible to dispose the rack so as to be inclined at a given angle even within the basin, and to move the rack up and down in this state. In such a case, it is desirable for the basin also to be given an inclined shape in keeping with the rack angle of inclination, and for the drive mechanism to move the rack in a direction parallel to the angle of inclination. By thus giving the basins, etc. such an inclined shape, each basin as a whole can be inclined without increasing the basin capacity, thus making it possible to reduce the amount of liquids used in cleaning and disinfection.

The endoscope reprocessor according to the first aspect of the invention is basically constituted as described above.

Next, an endoscope reprocessor according to the second aspect of the invention is described in conjunction with FIGS. 12A to 19B.

As is well known, endoscope reprocessors of various constructions are familiar to the art, including apparatuses designed so as to receive and reprocess all the component members of an endoscope within a basin, such as the endoscope reprocessor 210 described below and the endoscope reprocessor disclosed in JP 2006-68095 A, and apparatuses which have a construction wherein an elongated tubular cleaning pipe communicates with the basin and carry out cleaning by inserting the insertion tube of an endoscope into the cleaning pipe and receiving the other parts of the endoscope within the basin. The second aspect of the invention may be employed in apparatuses having either of these constructions.

Figure 12A:
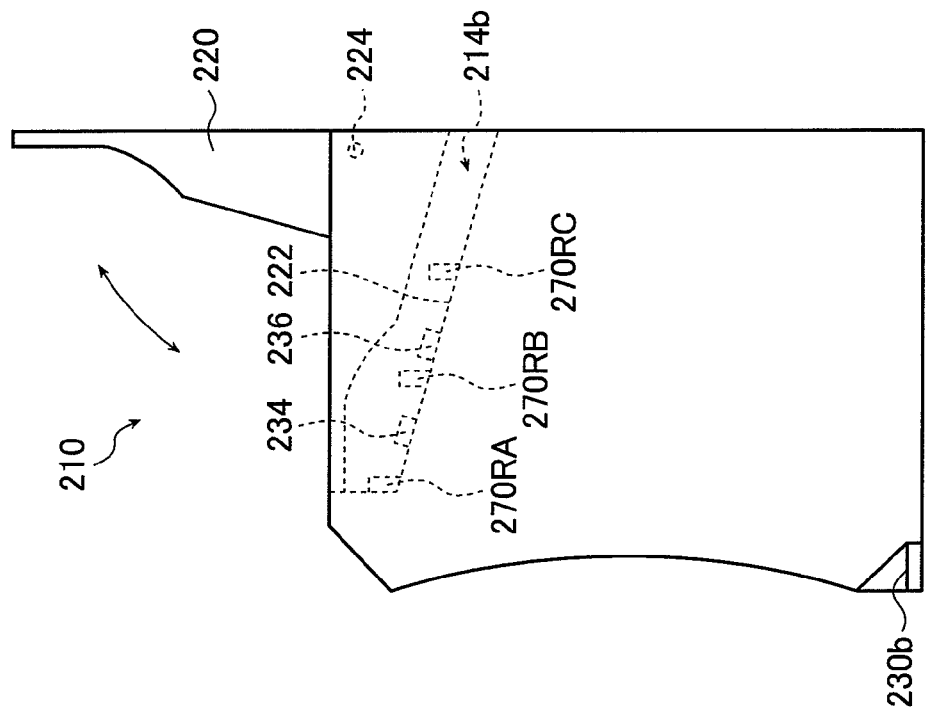
FIG. 12A is a perspective view schematically showing an embodiment of the endoscope reprocessor according to the second aspect of the invention.
Figure 12B:
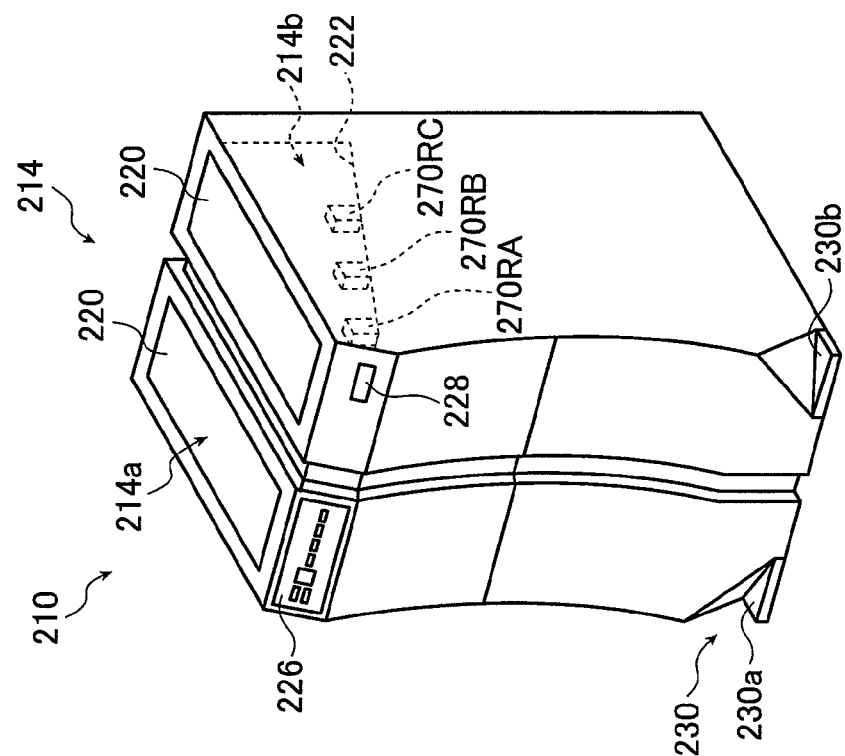
FIG. 12B is a side view of the endoscope reprocessor shown in FIG. 12A.
Figure 13:
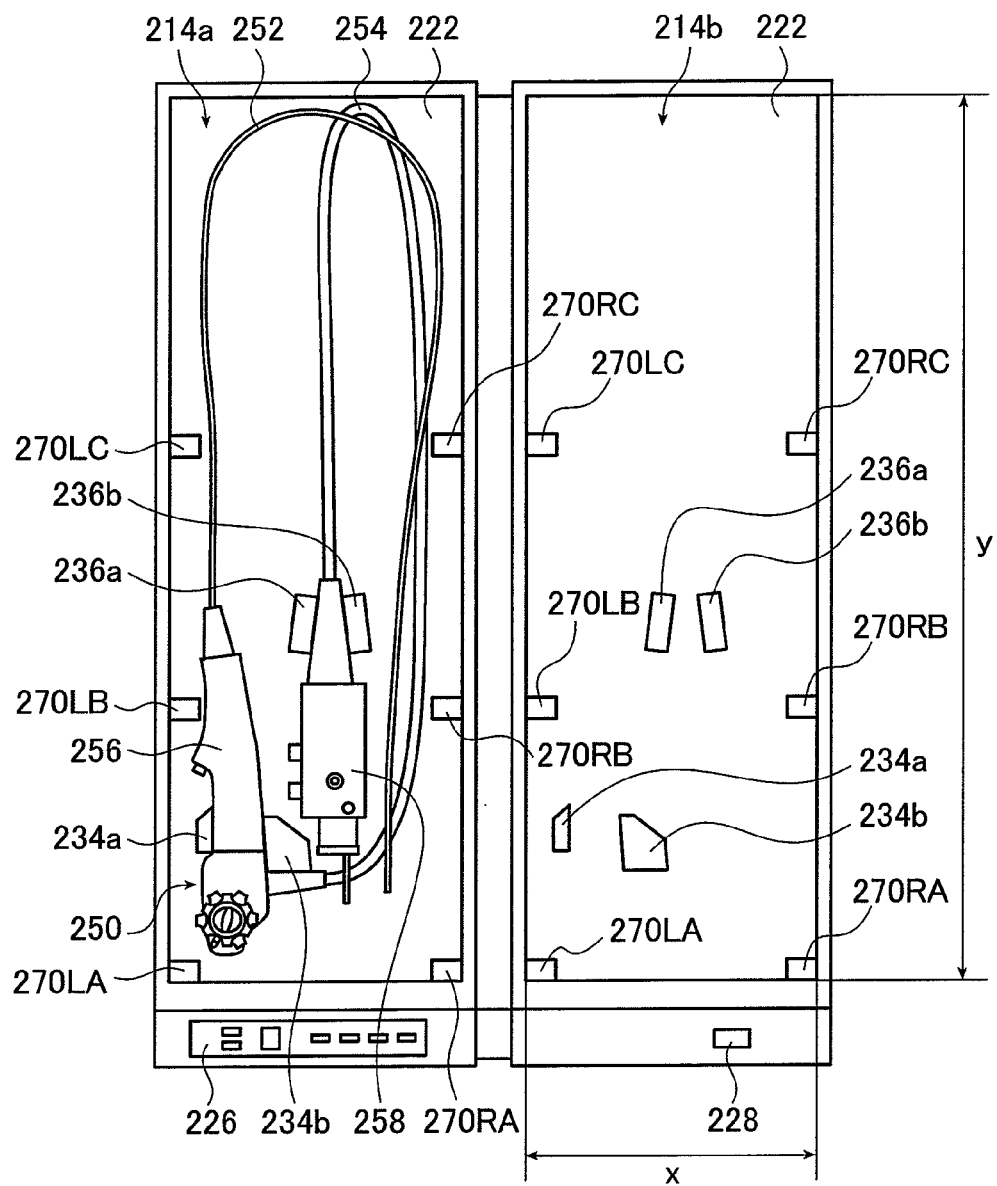
FIG. 13 is a schematic plan view of the top side of the endoscope reprocessor shown in FIG. 12A.

FIG. 12A is a perspective view schematically showing an embodiment of an endoscope reprocessor according to the second aspect of the invention. FIG. 12B is a side view of the endoscope reprocessor shown in FIG. 12A. FIG. 13 is a schematic top view (with the subsequently described lid 220 omitted) of this endoscope reprocessor.

The endoscope reprocessor 210 (also referred to below as "reprocessor 210") shown in FIGS. 12A and 12B is an apparatus for the automated cleaning and disinfection of an endoscope 250. This reprocessor 210 has two basins—a first basin 214a and a second basin 214b (also collectively referred to below as "the basin 214"), each adapted to receive and reprocess one endoscope 250, and is an apparatus capable of simultaneously, or asynchronously (independently) cleaning and disinfecting two endoscopes 250.

The endoscope reprocessor according to the second aspect of the invention may have a construction which can accommodate two or more endoscopes 250 in a single basin 214 and allows a plurality of endoscopes to be cleaned at the same time. However, when a plurality of endoscopes 250 are held in a single basin, the endoscopes 250 are stacked on top of one another, which may lower the cleanability and the ability to remove residual processing liquids (liquid detergent, liquid disinfectant, and tap water) by the subsequently described blowing of air. Hence, it is preferable for the endoscope reprocessor according to the second aspect of the invention to be configured so as to receive and reprocess a single endoscope per basin.

The reprocessor 210 of the illustrated embodiment has two basins 214. However, as noted above, the invention is not limited in this regard, and may have a single basin 214 or may have three or more basins 214. In addition, the direction in which the basins 214 are arrayed is not limited to the widthwise direction shown in the diagrams; a plurality of basins 214 may instead be arrayed in the lengthwise direction.

In the reprocessor 210, the first basin 214a and the second basin 214b each receive an endoscope 250 and carry out the reprocessing of the endoscope 250 by a process composed of three steps—a cleaning step in which cleaning with a liquid detergent and rinsing with tap water are carried out, a disinfecting step in which disinfection is carried out with a liquid disinfectant, and a rinsing step in which rinsing is carried out with tap water. In this endoscope reprocessor 210 according to the second aspect of the invention, the step of cleaning with liquid detergent and the post-cleaning rinsing step which are described above in connection with the endoscope reprocessor 10 according the first aspect of the invention are collectively referred to as the "cleaning step."

Moreover, the reprocessor 210 has tanks, pumps and fluid distribution lines for supplying detergent, disinfectant and the like to the first basin 214a and the second basin 214b. These are described in detail later in the specification.

In the reprocessor 210, because the first basin 214a and the second basin 214b have exactly the same construction, like members are assigned like reference symbols and reference is made primarily to "the basin 214" in the following description.

As noted above, each of the basins 214 (first basin 214a and second basin 214b) receives and cleans a single endoscope 250. Each is opened and closed at the top by a lid 220.

Although omitted in FIGS. 12A, 12B and 13 to enable the construction of the reprocessor 210 to be more clearly depicted, the basin 214 is provided at the interior with ports for connection to various channels (i.e., adapters or connectors thereof) of the endoscope 250, such as the forceps channel and the air/water supply channel, and with inlets for the introduction of liquid detergent and other processing liquids to the interior of the basin 214. These are described more fully later in the specification.

In the reprocessor 210 shown in the diagrams, the basin 214 has, according to a preferred embodiment, an elongated shape (planar shape as seen from above) and has an inclined bottom surface (floor) 222.

In this reprocessor 210, as shown in FIG. 13, the endoscope 250 is generally placed in the basin 214 with the insertion tube 252 and the universal cord 254 each folded in two (or more often, in the case of a long endoscope). The basin 214 holds a single endoscope 250, which is received on the inclined floor 222 thereof.

Also, in the reprocessor 210, as shown in FIG. 12B, the lid 220 pivots about a point of support 224, opening and closing the top of the basin 214.

Here, in a preferred arrangement, the reprocessor 210 shown in FIGS. 12A and 12B is provided, at a bottom side of the inclined floor 222, with the point of support (pivot point) 224 for opening and closing the lid 220. That is, in the reprocessor 210, the lid 220 rotates so that an end thereof at a top side of the inclined floor 222 moves up and down, thereby opening and closing the basin 214. In addition, control unit used for routine cleaning in the reprocessor 210, such as a control panel 226 for operating the reprocessor 210, a start button 228 for endoscope reprocessing, and foot pedals 230 (a pedal 230a for the first basin 214a, and a foot pedal for the second basin 214b) which open and close the lids 220 are provided at the top side (top end) of the floor 222 of the basin 214 (preferably near the basin 210 end at the top side of the floor 222 and/or on the basin 210 endface at the top side of the floor 222)

That is, in a preferred embodiment of the reprocessor 210, the lid 220 opens and closes at the top side of the inclined floor 222, and this top side is the side where various endoscope 250 reprocessing operations are carried out. The surface of the basin 214 on the top side of the floor 222 is also referred to below as the "front surface."

In the second aspect of the invention, the side of the floor 222 higher than the center thereof in the lengthwise direction is referred to as the "top side," and the side lower than the center is referred to as the "bottom side."

The endoscope reprocessor according to the second aspect of the invention is not limited to arrangement in which the top side of the floor is located at the front surface side of the basin; arrangement in which the bottom side of the floor is located at the front surface side of the basin are also possible.

Also, opening and closing of the lid are not limited to being carried out in the lengthwise direction of the basin. An arrangement in which the lid is opened and closed in the widthwise direction of the basin is also possible. In such a case, a side of the basin in the widthwise direction may be used as the side where various operations are carried out (front surface).

In addition, the lid is not limited to an arrangement which opens and closes by pivoting about a point of support, and may alternatively be, for example, a sliding-type lid (shutter). In such a case, when the shutter opens and closes in the lengthwise direction of the basin, it is preferable for the shutter to be constructed so as to open from the top side of the basin floor. Similarly, it is preferable that the near side of the basin to the operator serve as the side where various operations are carried out (front surface).

In a preferred embodiment of the reprocessor 210 shown in the diagrams, the basin 214, by having such an elongated construction with the floor inclined in the lengthwise direction, allows setting of the endoscope 250 to be reprocessed in the reprocessor 210, i.e., placement of the endoscope 250 at a given position in the basin 214, to be carried out easily and quickly.

Generally, when an endoscope 250 is to be carried by hand, the control unit 256 and the connector 258 are arranged as the ends, the long insertion tube 252 and universal cord 254 are folded in two (or more often), and the endoscope 250 is carried about while holding both ends. Therefore, by giving the basin 214 an elongated construction with an inclined floor 222, it is possible, using gravity, to more or less drop the endoscope 250 into the basin 214 with the doubled-up side first in the manner in which it has been carried over, that is, without having to carry out any cumbersome tasks such as coiling the insertion tube 252, thus enabling the endoscope 250 to be properly set within the basin 214 rapidly, easily and with little physical exertion. Particularly in an arrangement where the top side of the inclined floor 222 is the front surface side of the apparatus where control is carried out, and the endoscope 250 is set with the control unit 256 and connector 258 on the front surface side, the endoscope 250 may be inserted into the basin 214 by placing the heavier control unit 256 and connector 258 on the floor 222 closest to the operator and dropping in the insertion tube 252 and universal cord 254, enabling the endoscope 250 to be very quickly and easily set into the basin 214.

Also, as described subsequently, the reprocessor 210 has a blowing unit 270 (see FIGS. 15A to 15C) which blows a gas such as air into the basin 214. Every time a cleaning, disinfecting or rinsing step ends, the blowing unit 270 blows a gas into the basin 214, and more specifically onto the inside walls of the basin 214, the outer surface of the endoscope 250, and the underside of the lid 220, thereby removing residual processing liquids. Here, because the basin 214 thus has the inclined floor 222, blowing the gas from the top side to the bottom side of the floor 222 enables the efficient removal and recovery, using gravity, of processing liquids from the outer surface of the endoscope 250 and elsewhere.

The inclination of the floor 222 of the basin 214 is not subject to any particular limitation. However, based on investigations by the inventors, the difference in vertical height between the top end and the bottom end of the floor 222 in the lengthwise direction is preferably from about 20 to about 40 cm, and more preferably from about 29 to about 35 cm.

By imparting such an inclination to the floor 222 of the basin 214, the effects of inclining the floor 222 can be desirably manifested, in addition to which the loading of the endoscope 250 in the basin 214 and the removal and recovery of processing liquids can be more efficiently carried out.

In the second aspect of the invention, when the floor 222 of the basin 214 is inclined, the shape of the floor is not limited to a single planar shape. For example, the floor 222 may have a shape with regions of differing pitch (angle with respect to the horizontal direction), such as one made up of an array of a plurality of flat planes of different angles, a curved shape that is upwardly convex (out-curled) or a curved shape that is upwardly concave (in-curled).

Figure 14:
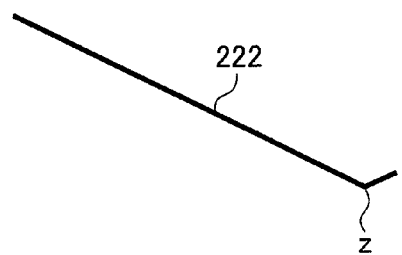
FIG. 14 is a schematic diagram showing another example of the bottom surface shape of the endoscope reprocessor according to the second aspect of the invention.

Alternatively, as shown schematically in FIG. 14, the floor 222 of the basin 214 may have, near the lower end, a pit for improving ease of drainage from the basin 214. In such a case, the floor 222 of the basin 214 is substantially that portion up to the lowest point z which forms the pit.

In cases where the basin 214 has an elongated shape (planar shape), the size x in the width direction and the size y in the lengthwise direction of the basin 214 (the region which receives the endoscope 250) are not subject to any particular limitation (see FIG. 13). Therefore, the size of the basin 214 may be suitably set according to the type of endoscope 250 to be reprocessed. Here, in the second aspect of the present invention, an "elongated basin 214" refers to a basin 214 which has a size x in the width direction of preferably not more than 40 cm, and more preferably from about 20 to about 40 cm, and has a length-to-width size ratio (length direction/width direction, y/x) of preferably at least 2, and more preferably at least 4.

As a result of investigations by the inventors, by giving the basin 214 an elongated shape such as that described above, the basin 214 can easily accommodate substantially all types of endoscopes 250 currently in use. Moreover, the reprocessor 210, even if it has a plurality of basins 214, can be appropriately kept from becoming needlessly large.

In addition, in the second aspect of the invention, when the basin is elongated, the shape is not limited to a rectangular shape like that shown in the diagrams. For example, any of various shapes may be used, including trapezoidal shapes, elliptical shapes, and barrel-like shapes in which the long sides of a rectangle curvilinearly bow outward.

In cases where the basin has a shape other than a rectangular shape, the size of the basin may be such that, for example, if one imagines the smallest rectangle within which the basin, in accordance with its shape, can be inscribed, letting the lengthwise direction of the rectangle serve as the lengthwise direction of the basin, the length of the long sides of the rectangle is the size y of the basin in the lengthwise direction and the length of the short sides of the rectangle is the size x of the basin in the width direction.

In the endoscope reprocessor of the second aspect of the invention, the shape of the basin (planar shape) is not limited to one that is elongated as shown in the diagrams, and may be, for example a shape for which the ratio y/x is less than 2, a circular shape or a square shape.

It is preferable for the floor (the surface which holds (supports) the endoscope) to be inclined in one direction.

The height of the basin 214 (the height at the top end (edge) of the basin 214), while not subject to any particular limitation, is preferably from about 60 to about 100 cm, and more preferably from about 70 to about 90 cm.

According to investigations by the inventors, by setting the height of the basin 214 in the above range, in an arrangement where the various operations are carried out with the lengthwise direction of the basin 214 serving as the front surface, it is possible for even an operator having a short height to easily set the endoscope 250 in the reprocessor 210.

In the reprocessor 210 shown in the diagrams, the endoscope 250 is set in the basin 214 (received at a predetermined position) by being placed onto the floor 222.

It is preferable here for the basin 214 to have on the floor 222 thereof (the floor 222 is preferred, although the inside walls of the basin 214 are also possible) positioning unit for positioning various parts of the endoscope 250, such as the control unit 256, the connector 258, the universal cord 254, and the insertion tube 252. In particular, because it is preferable, as mentioned earlier, to set the endoscope 250 by positioning the control unit 256 and the connector 258 of the endoscope 250 on the top side of the floor 222, the floor 222 preferably has on the top side thereof positioning unit for the control unit 256 and the connector 258 of the endoscope 250.

The basin 214 shown in the diagrams has, set upright on the top side of the floor 222, engaging members 234 (234a and 234b) for engaging, supporting from below and positioning the control unit 256 of the endoscope 250, and engaging members 236 (236a and 236b) for similarly engaging, supporting from below and positioning the connector 258. Accordingly, the endoscope 250 is set in a given position in the reprocessor 210, i.e., the basin 214 (floor 222), by having the control unit 256 positioned by the engaging members 234a, 234b and by having the connector 258 positioned by the engaging members 236a, 236b.

With such endoscope positioning unit, it is possible for the endoscope 250 to be properly set, both easily and quickly, in the reprocessor 210 (the basin 214). Moreover, as briefly noted earlier, every time one of the steps in endoscope reprocessing ends, the reprocessor 210 blows air into the basin 214 from the blowing unit 270 so as to remove processing liquids remaining on the inside walls of the basin 214 and the outer surface of the endoscope 250. With such endoscope positioning unit, the endoscope 250 can be properly set in the basin 214, thereby making it possible to stabilize the blowing of air onto the endoscope 250 and thus enable even better removal of residual processing liquids.

Various known unit may be used as the unit for positioning various parts of the endoscope 250 (e.g., the control unit 256 and the connector 258) which are provided on the floor 222 or elsewhere.

Illustrative examples include recesses which loosely fit or receive specific sites on the control unit or the like, engaging members which positively engage various portions of the endoscope 250, and hooks or engaging members which, as shown in the diagrams, engage and support from below the control unit 256 or the like that falls into place along the slope of the floor 222. Such positioning unit may also function as unit for securing various portions of the endoscope, or specialized unit for securing various portions of the endoscope 250 may also be present in addition to the positioning unit.

The endoscope reprocessor according to the second aspect of the invention has a blowing unit for blowing a gas into the basin, and uses the blowing unit to blow a gas into the basin each time any of the various steps in endoscope reprocessing (cleaning step, disinfecting step, rinsing step) ends.

In the reprocessor 210 shown in the diagrams, six blowing unit 270 stand upright on the floor 222 of the basin 214. The blowing unit 270 blow air into the basin 214 interior (inside walls of basin 214, outer surface of endoscope 250, underside of the lid 220) each time one of the reprocessing steps ends—i.e., the cleaning step in which the endoscope 250 is cleaned with liquid detergent and rinsed with tap water, the disinfecting step in which the endoscope 250 is disinfected with liquid disinfectant, and the rinsing step in which the endoscope 250 is rinsed with tap water.

Moreover, in the present aspect of the invention, each of the cleaning, disinfecting and rinsing steps of endoscope reprocessing is carried out in order by the control of pumps, solenoid valves and heaters using the same types of control unit (not shown) as the controller 18, and especially the CPU 32, the input/output control circuit 38 and the load driving circuit 48, shown in FIG. 8. The blowing of a gas into the basin by a blowing unit carried out each time a step ends also is carried out by using similar control unit to control the blowing unit.

In the reprocessor 210 according to the second aspect of the invention, by using such blowing unit 270 to blow air into the basin 214 each time a processing step ends, processing liquids remaining on the inside walls of the basin 214 (referred to below as "basin inside walls"), the outer surface of the endoscope 250 (referred to below as "endoscope outer surface") and the underside of the lid 220 (referred to below as the "lid underside") can be removed after the end of each step.

In this way, the degradation and loss of liquid disinfectant which is used repeatedly a given number of times can be suppressed, and the endoscope reprocessing time can be shortened.

In the second aspect of the invention, the gas blown into the basin is not limited to air. Suitable use can be made of various types of gas, such as inert gases (e.g., nitrogen, argon), so long as they do not have an adverse effect on the endoscope outer surface or the reprocessor and do not react with the processing liquids. From the standpoint of running costs, the use of air is preferred.

In the illustrated embodiment, three blowing unit 270 (270RA, 270RB and 270RC (also referred to collectively as 270R)) are disposed in a row from the top to the bottom end of the floor 222 inside the basin 214 near the right edge as seen from the front, and three blowing unit 270 (270LA, 270LB and 270LC (also referred to collectively as 270L)) are disposed in a row from the top to the bottom end of the floor 222 inside the basin 214 near the left edge as seen from the front.

Moreover, the blowing unit 270 all blow air in a direction oriented from above to below in the direction of inclination of the floor 222. In this way, using the inclined floor 222, processing liquids remaining on the endoscope outer surface and elsewhere can be reliably removed gravitationally.

In the second aspect of the invention, the number of blowing unit 270 is not limited to six, and may be five or fewer or seven or more. Also, the positions of the blowing unit 270 are not limited to being arranged on both the left and right sides of the basin 214 and in the direction of inclination by the floor 222.

That is, the positions and number of blowing unit 270 may be suitably set so as not to interfere with the reception and cleaning of the endoscope 250 within the basin 214 and so as to be able to suitably blow air throughout the inside walls of the basin, the outer surface of the endoscope and the underside of the lid. Accordingly, the blowing unit 270 may be disposed at positions on, for example, the inner side walls of the basin 214 or the underside of the lid, or may be disposed at two or more positions on the floor 222, the basin 214 side walls and the lid underside as in an arrangement that provides blowing unit 270 on the floor 222 and the lid underside.

However, when the floor 222 is inclined in the manner of the basin 214 shown in the diagrams, it is preferable for there to be a plurality of blowing unit 270 arrayed above to below, and for the blowing unit 270 to blow air (gas) in a direction oriented from above to below.

Figure 15A:
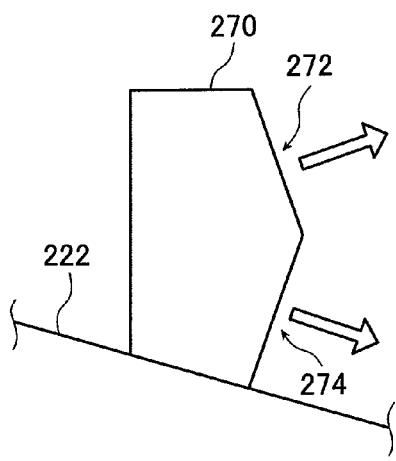
FIG. 15A is a schematic side view of the blowing unit in the endoscope reprocessor shown in FIG. 12A.
Figure 15B:
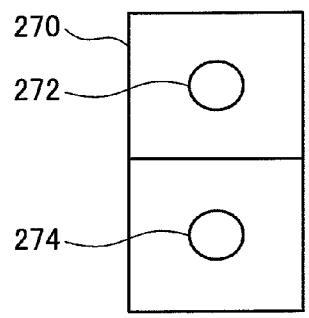
FIG. 15B is a front view of the same.
Figure 15C:
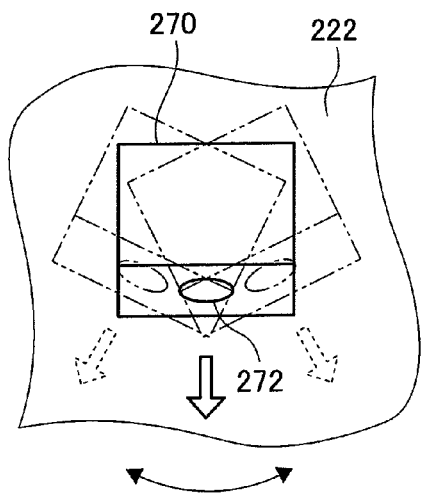
FIG. 15C is a plan view of the same.

FIGS. 15A to 15C schematically show the blowing unit 270.

FIG. 15A is a side view (taken in the same direction as in FIG. 12B), FIG. 15B is a view looking up from below the floor (as seen from the front), and FIG. 15C is a top view (taken in the same direction as in FIG. 13).

In the endoscope reprocessor of the second aspect of the invention, the blowing unit which blows air into the basin 214 after each step of the endoscope cleaning and disinfecting process ends is not limited to those embodiments shown in the diagrams. Use may be made of any unit for blowing the gas.

As shown in FIG. 15A, the blowing unit 270 has two air nozzles 272 and 274 arranged vertically on the surface at the bottom side of the floor 222.

As shown in FIG. 15A, the upper air nozzle 272 blows air upward, and the lower air nozzle 274 blows air downward. In the illustrated embodiment, air is thereby blown against not only the basin inside walls and the endoscope outer surface, but also against the lid underside, thereby enabling the removal of residual processing liquids.

Moreover, as indicated by the chain double-dashed lines in FIG. 15C, the blowing unit 270 is constructed so that when it blows air, it oscillates back-and-forth laterally (in the left-right direction as seen from the front), thereby laterally changing the air blowing direction. This makes it possible to remove processing liquids remaining on the basin inside walls, the endoscope outer surface and the lid underside by blowing air evenly inside the basin 214. The method of oscillating the blowing unit 270 is not subject to any particular limitation; any of various known methods may be used.

In the reprocessor 210 according to the second aspect of the invention, the blowing unit 270 is not limited to having two air nozzles—an upward air nozzle 272 and a downward air nozzle 274, and may instead have only one air nozzle. However, having an upward air nozzle and a downward air nozzle as in the illustrated embodiment is desirable because processing liquids remaining not only on the endoscope outer surface and the basin inside walls, but also on the lid underside, can be removed.

Moreover, the blowing unit 270 is not limited to varying the blowing direction laterally; the blowing unit 270 may be constructed so as to vary the air blowing direction in the vertical direction as well as laterally, or may be constructed such that the lateral direction is fixed and the air blowing direction changes only in the vertical direction. Alternatively, the air blowing direction may be fixed, although it is preferably variable because this enables air to be blown evenly over the interior of the basin 214.

As shown in the piping diagram in FIG. 16 and in the subsequently described piping diagram for the reprocessor 210 in FIG. 17, an air pump 316 for supplying air to the respective channels of the endoscope 250 is connected to the blowing unit 270 via valves 400 (valves 400RA, 400RB and 400RC (also collectively referred to as "400R"), and valves 400LA, 400LB and 400LC (also collectively referred to as "400L")) which correspond to each blowing unit 270. In addition, a valve 160 (160a or 160b) for switching the supply of air to the first basin 214a and the second basin 214b is disposed between the air pump 316 and the valves 400.

Specifically, the valve 400RA is connected to the blowing unit 270RA, the valve 400RB is connected to the blowing unit 270RB, and the valve 400RC is connected to the blowing unit 270RC. Likewise, the valve 400LA is connected to the blowing unit 270LA, the valve 400LB is connected to the blowing unit 270LB, and the valve 400LC is connected to the blowing unit 270LC.

Figure 16:
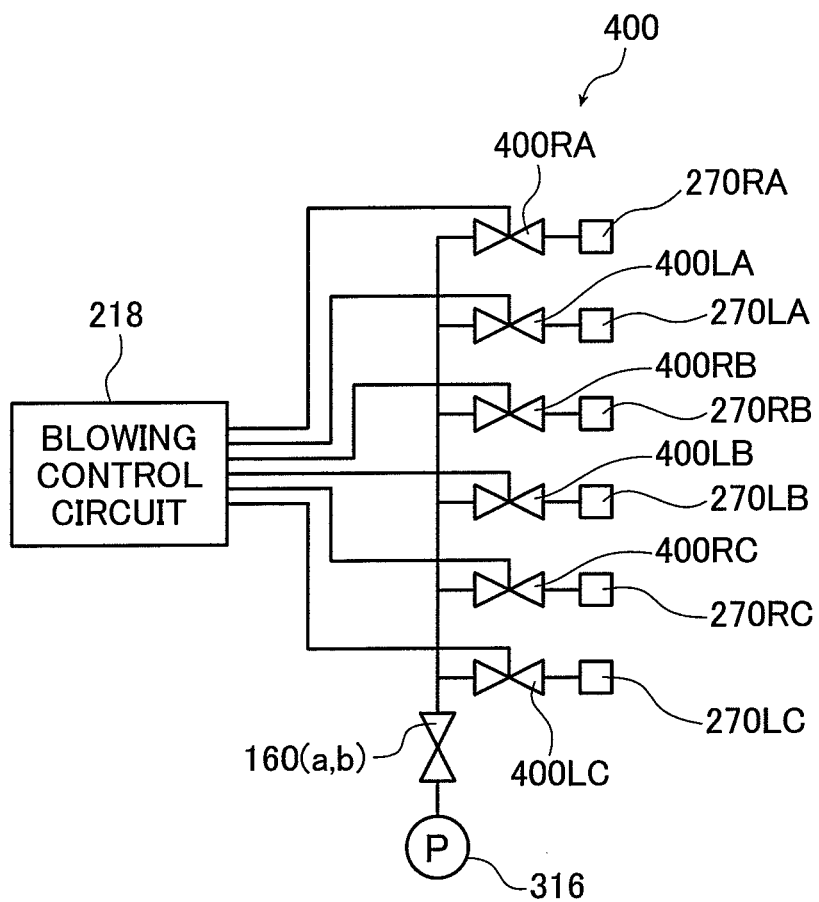
FIG. 16 is a schematic piping diagram showing an example of the lines for the blowing unit in the endoscope reprocessor shown in FIG. 12A.
Figure 17:
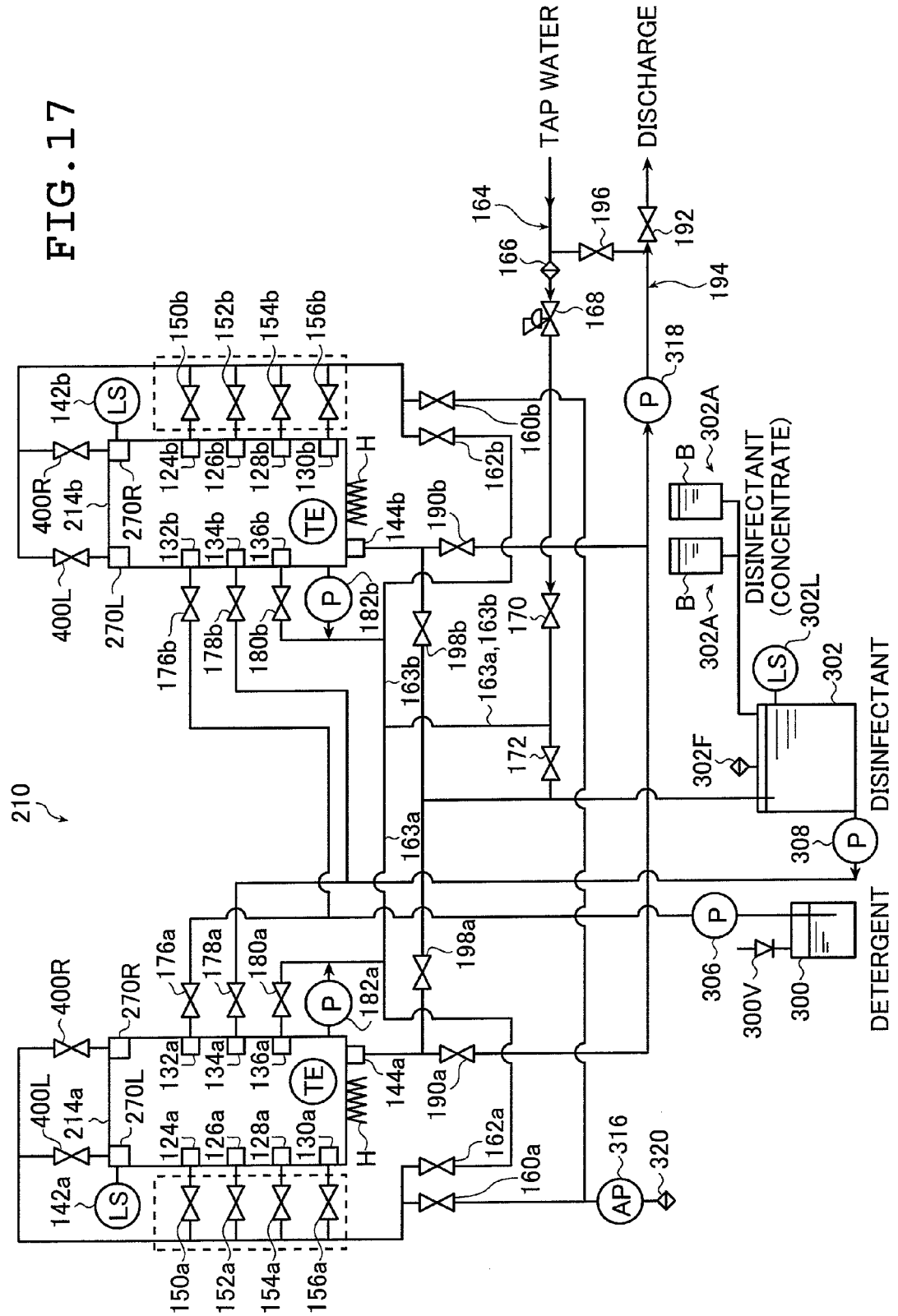
FIG. 17 is a schematic piping diagram showing an example of the lines in the endoscope reprocessor shown in FIG. 12A.

To enable the arrangement to be more readily understood, FIG. 16 shows in simplified form only the path from the air pump 316 to the blowing unit 270, and FIG. 17 shows only the valves 400L and valve 400R and only the blowing unit 270L and 270R.

Therefore, in the reprocessor 210 shown in the diagrams, according to a preferred embodiment, as shown in FIG. 16 for example, a blowing control circuit 218 is provided within a control unit similar to the controller 18 shown in FIG. 8, for example, and controls each individual valve 400 (440RA, 400RB, 400RC, 400LA, 400LB and 400LC), enabling the blowing of air into the basin 214 by each blowing unit 270 to be controlled.

The second aspect of the invention is not limited in this regard. Any of various arrangements may be employed to control the blowing of air from the respective blowing unit 270. For example, in one suitable arrangement, by having the topmost blowing unit 270RA and 270LA serve as one pair, the intermediate blowing unit 270RB and 270LB serve as another pair, and the bottommost blowing unit 270RC and 270LC serve as yet another pair, the blowing of air can be controlled separately for each pair. In another possible arrangement, instead of carrying out control of the respective blowing unit 270 separately, the blowing of air may be controlled collectively for all of the blowing unit 270.

In the reprocessor 210 shown in FIG. 17, the air pump 316 for supplying air to each channel of the endoscope 250 is used as an air supply source for the blowing unit 270 that blows air into the basin 214.

In the reprocessing of the endoscope 250, it is necessary to supply processing liquids also to channels within the endoscope 250, such as the forceps channel and the air/water supply channel, and to carry out the cleaning and disinfection of these channels. The reprocessor 210 thus has an air supply source for supplying air to the channels in order to discharge processing liquids from the channels.

In the endoscope reprocessor according to the second aspect of the invention, the air supply source to the blowing unit 270 may be separately provided. However, utilizing the air supply source to the channels of the endoscope 250, as in the reprocessor 210 shown in the diagrams, is desirable for holding down increases in the cost and size of the endoscope reprocessor.

In the reprocessor 210 according to the second aspect of the invention, no particular limitation is imposed on the order in which air blowing is carried out by the respective blowing unit 270.

For example, air blowing may be carried out by all the blowing unit 270 at once. Alternatively, air blowing may be carried out first by the blowing unit 270R on the right side, then by the blowing unit 270L on the left side.

In cases where the reprocessor 210 has, as shown in the diagrams, an inclined floor 222 and has blowing unit 270 arrayed in the direction of inclination, it is preferable for air blowing to begin sequentially from the blowing unit 270 situated at the top.

That is, first, air blowing is carried out by the topmost blowing unit 270RA and 270LA. Next, blowing by the topmost blowing unit 270RA and 270LA is either continued or stopped, and air blowing by the intermediate blowing unit 270RB and 270LB is started. Next, air blowing by the intermediate blowing unit 270RB and 270LB is continued or stopped, and air blowing by the bottommost blowing unit 270RC and 270LC is started.

In this way, by starting the blowing of air in order from the top blowing unit 270, the processing liquid removal effects using gravitational drainage can be better achieved, making it possible to more efficiently and reliably carry out the removal of processing liquids.

In the reprocessor 210 according to the second aspect of the invention, conditions such as the air flow rate, blowing velocity and blowing time are not subject to any particular limitation. The conditions that enable the proper removal of processing liquids remaining on the endoscope outer surface and the basin inside walls following the end of each step may be set as appropriate based on such considerations as the type and size of the endoscope 250 to be reprocessed, the size and shape of the basin 214, and the required cleaning ability (cleansing power and treatment time).

The endoscope 250 components having the largest amount of residual processing liquid and for which the removal of such liquids is the most difficult, are the control unit 256 and the connector 258, both of which are of complex shape.

Therefore, in the endoscope reprocessor according to the second aspect of the invention, the air blowing times to the control unit 256 and connector 258 may be longer than the air blowing times for the insertion tube 252 and the universal cord 254. That is, in the case of the reprocessor 210 shown in the diagrams, because the endoscope 250 is set in the reprocessor 214 with the control unit 256 and the connector 258 situated uppermost, the blowing of air from the respective blowing unit 270 may be controlled so that the blowing time by the topmost blowing unit 270RA and 270LA is longer than for the other blowing unit 270.

As described above, in the reprocessor 210, by having such a blowing unit 270 and blowing air into the basin 214 each time the respective cleaning, disinfecting and rinsing steps end, processing liquids remaining on the basin inside walls, endoscope outer surface and lid underside can be removed following the end of each step (following discharge of the processing liquid from the basin 214).

In this way, degradation and loss of the disinfectant which is recovered and repeatedly used until the completion of a predetermined number of cleaning cycles can be suppressed, and the reprocessing time can be shortened.

Specifically, by blowing air into the basin 214 after the cleaning step has ended, tap water remaining on the endoscope outer surface and elsewhere can be removed and discharged, preventing the disinfectant used in the next step from being diluted/degraded by tap water. In some cases where rinsing with tap water or the like is not carried out after cleaning with detergent; in such cases, disinfectant dilution/degradation/deterioration by the admixture of detergent with the disinfectant can be suppressed.

Moreover, by blowing air into the basin 214 following the end of the disinfecting step, disinfectant remaining on the endoscope outer surface and elsewhere can be removed and recovered, thus increasing the percent recovery of the disinfectant and minimizing a loss of disinfectant.

Also, by blowing air into the basin 214 following the end of the rinsing step, the tap water remaining on the endoscope outer surface and elsewhere can be removed and discharged, thus making it possible, without manual wiping or the like, to avoid wetting of the reprocessor 210 vicinity from dripping water when the endoscope 250 is removed from the basin 214 following the end of reprocessing. Each step in the cleaning and disinfecting process will be described subsequently in greater detail.

In addition, because processing liquids remaining on the basin inside walls and the endoscope outer surface can be removed by blowing air into the basin 214, after the processing liquids have been discharged from the basin 214, there is no need for a so-called draining period, thus making it possible to shorten the endoscope reprocessing time.

As mentioned above, the disinfectant used to disinfect the endoscope is recovered and reused until a predetermined number of reprocessing cycles have been carried out, following which it is discarded and replenished with fresh disinfectant. In prior-art endoscope reprocessors, when a processing liquid such as the detergent is discharged from the basin and the current step ends, the next step begins without any intervening operation such as rinsing and air blowing, and the next processing liquid such as the disinfectant is immediately supplied to the basin. As a result, processing liquid ends up remaining at the interior of the basin and on the endoscope outer surface. This residual processing liquid dilutes/degrades the disinfectant, lowering its disinfecting ability. Moreover, because desirable recovery of the disinfectant is impossible (low recovery ratio), a loss of disinfectant occurs, making it necessary to supply a larger amount of disinfectant in order to offset such loss.

Also, in prior-art endoscope reprocessors, to carry out discharge somewhat more reliably following the end of each step, a drain time is provided after discharge from the basin.

By contrast, according to the second aspect of the invention, degradation and loss of the disinfectant can be suppressed to a suitable degree in the manner described above.

Hence, with the reprocessor 210 according to the second aspect of the invention, it is possible to stably carry out proper reprocessing of the endoscope 250, in addition to which the amount of disinfectant used (filling amount) is reduced, which helps to hold down the operating costs. Moreover, the length of time required for reprocessing the endoscope 250 is shortened, enabling rapid, efficient cleaning and disinfection to be carried out even in cases where the endoscope 250 must be repeatedly used.

In the reprocessor 210 according to the second aspect of the invention, no particular limitation is imposed on the shape of the lid 220 on the basin 214. Any lid configuration or shape adapted to the shape of the basin 214 may be employed, provided the lid 220 is capable of closing the basin 214, preferably in a substantially airtight manner, and most preferably in an airtight manner.

In the reprocessor 210 shown in the diagrams, the opening and closing of the lid 220 is carried out, as in various types of endoscope reprocessors, by a foot pedal 230 provided on the front side of the reprocessor 210. Known unit used in various endoscope reprocessors may be employed to open and close the lid 220 with the foot pedal 230.

Here, in the second aspect of the invention, the lid 220 is not simply a plate-like member. Preferably, it has a region on the side facing the floor 222 of the basin 214 (referred to below as the underside of the lid 220), which region, when the lid 220 is closed, is inclined in the same direction as the floor 222.

As shown in FIG. 12B, it is especially preferable for the region which is formed on the underside of the lid 220 and is inclined in the same direction as the floor 222 to be parallel or substantially parallel to the floor 222 when the lid 220 is closed.

In light of concerns over the operating costs of the reprocessor 210 and environmental contamination, it is desirable for the amount of processing liquid used in each step to be on the low side.

To properly carry out reprocessing, the endoscope 250 must be entirely immersed in the processing liquid.

However, in the reprocessor 210 of the present embodiment, because the floor 222 of the basin 214 is inclined as described above, even the empty space (i.e., space where the endoscope 250, when loaded into the basin 214, is not present) above the bottom end of the floor 222 must be filled with the processing liquid. Being that this space is wasted space, the processing liquid that fills this region is, in a sense, unnecessary processing liquid.

When endoscope 250 reprocessing is carried out under these conditions in the reprocessor 210 shown in the diagrams, because the detergent is discarded after each cleaning step, a large amount of detergent ends up being needlessly used. Also, the disinfectant is generally used and reused for only a given number of cleaning cycles. However, in recent years, to achieve a higher degree of hygienic control and more reliably prevent infection, it is often desirable to reprocess the endoscope 250 in a single shot by discarding the disinfectant after each use. In such cases, large amounts of disinfectant end up being needlessly used.

To overcome this problem, as shown in FIG. 12B, the underside of the lid 220 can be given an inclination which matches the inclination of the floor 222; that is, the underside of the lid 220 can be given a protruding shape (i.e., a shape having a convex feature) which is inclined in the same direction as the inclination of the floor 222, thereby enabling wasted space at the top of the basin 214 interior where the endoscope 250 is not present to be filled by the lid 220.

Therefore, by using the lid 220 having such a construction, it is possible to reprocess the endoscope 250 with a small amount of processing liquid, enabling a reprocessor 210 which does not needlessly use processing liquid and has low operating costs and an excellent environmental performance to be achieved. In particular, as shown in FIG. 12B, by providing the underside of the lid 220 with a region that is parallel or substantially parallel to the floor 222, it is possible to more suitably fill wasted space with the lid 220.

The region on the underside of the lid 220 which is inclined in the same direction as the floor 222 is preferably located in a region corresponding to the bottom side of the inclined floor 222. It is especially preferable for the inclined region on the underside of this lid 220 to be located at the top of the region where only the insertion tube and the universal cord of the endoscope 250 are present when the endoscope 250 has been set at a predetermined position in the basin 214.

Moreover, to suitably reduce the amount of processing liquids, it is desirable, of course, for the region at the underside of the lid 220 which is inclined in the same direction as the floor 222 to be as large as possible in the width direction. In particular, in the width direction of the basin 214 (at the interior thereof), the lid 220 protrusion which is the region inclined in the same direction as the floor is preferably sized so as to liquid-tightly fit into, or to provide a loose fit with, the inside walls of the basin 214.

When the lid 220 having a thus inclined underside is used, there is a possibility that the amount of processing liquid attached to the lid underside will increase following the end of each step. However, according to the second aspect of the invention, because air is blown into the basin 214 by the blowing unit 270 after the end of each step, the degradation or loss of disinfectant owing to processing liquids attached to the lid underside, and other undesirable effects such as the dripping of liquid from the lid 220, can be effectively suppressed.

The lid 220 may be made of any material, provided it has a sufficient resistance to processing liquids such as detergent and disinfectant.

It is preferable here for the lid 220 to be transparent so that the operator can see the interior of the basin 214 when the lid 220 on the basin 214 is closed.

FIG. 17 is a schematic diagram of the fluid distribution system in the illustrated endoscope reprocessor 210.

As mentioned above, the reprocessor 210 has two basins—a first basin 214a and a second basin 214b.

However, the reprocessor 210 shown in the appended diagrams has only one each of the tanks which hold the processing liquids for carrying out reprocessing of the endoscope, i.e., the detergent tank 300 which holds liquid detergent and the disinfectant tank 302 which holds liquid disinfectant. That is, these tanks are shared by the first basin 214a and the second basin 214b. Moreover, the reprocessor 210 has only one detergent pump 306 for supplying liquid detergent to the basins 214a and 214b from the detergent tank 300, and only one disinfectant pump 308 for supplying liquid disinfectant to the basins 214a and 214b from the disinfectant tank 302. Hence, each of these pumps is shared by the first basin 214a and the second basin 214b.

Although any of various types of known pumps may be used as these pumps, the use of metering pumps is of course preferred. In cases where the respective tanks are positioned below the basins 214a and 214b, it is preferable to use self-priming metering pumps such as diaphragm pumps.

In addition, the reprocessor 210 has only one air pump 316 for supplying air to, and only one discharge pump 318 for discharging processing liquids from, the respective channels of the endoscope 250. These pumps are shared by the two basins 214a and 214b. An air filter 320 is provided at the air inlet to the air pump 316.

Hence, the reprocessor 210 is an apparatus which has two basins—the first basin 214a and the second basin 214b, and is capable of cleaning two endoscopes 250, either simultaneously or asynchronously. The tanks for holding processing liquids such as liquid detergent and the pumps for supplying the processing liquids are each shared by the two basins 214a and 214b.

In the reprocessor 210, although each pump and tank is shared between the first basin 214a and the second basin 214b, in order to carry out reprocessing in the first basin 214a and the second basin 214b independently and asynchronously, as shown in FIG. 17, the two basins 214a and 214b have mutually independent plumbing.

In addition to the above, the reprocessor 210 according to the second aspect of the invention may also have pumps, tanks, fluid distribution lines and the like for carrying out various kinds of processing.

For example, to carry out water leak detection on the endoscope 250, the reprocessor 210 may have air pumps for applying air pressure to the interior of the insertion tube 252 and the universal cord 254, air ports for connecting to an adapter (connector) and introducing air into the insertion tube 252 and the universal cord 254, and lines for connecting to the air port and the air pump.

Moreover, as with the earlier described reprocessor 10 according to the first aspect of the invention, the reprocessor 210 of the present embodiment may also have an alcohol tank for introducing alcohol into the various channels of the endoscope after cleaning and disinfection have ended and carrying out alcohol flushing to accelerate drying, an alcohol pump for supplying alcohol, and lines for connecting the alcohol pump to each of the subsequently described ports.

In the illustrated embodiment, the disinfectant tank 302 is provided with a level sensor 302L for measuring the amount of liquid disinfectant in the tank, and mounts 302A for disinfectant bottles B filled with liquid disinfectant which supply liquid disinfectant to the disinfectant tank 302. In the embodiment shown in FIG. 17, two mounts 302A have been provided for the purpose of illustration. The disinfectant tank 302 also is provided with a deodorizing filter 302F for preventing the disinfectant odor from leaking to the exterior.

The detergent tank 300 is provided with a check valve 300V to prevent the unintended discharge of liquid detergent from the detergent tank 300.

The disinfectant tank 302 and its vicinity have substantially the same construction as the disinfectant tank 102 and its vicinity in the above-described reprocessor 10 according to the first aspect of the invention.

Because the first basin 214a and the second basin 214b are basically of like construction and the fluid distribution systems for each are largely the same, the description of the first basin 214a that follows generally applies also to the second basin 214b. Descriptions concerning the second basin 214b will be provided as needed.

Also, aside from the inclusion of blowing unit 270, the plumbing for the reprocessor 210 is largely the same as that for the reprocessor 10 according to the first aspect of the invention shown in FIG. 7. Accordingly, in the description that follows, components having like functions are assigned like names and reference symbols, and detailed explanations are omitted. It should be noted that the alcohol tank and the check valve associated therewith are omitted from the diagram. In the reprocessor 210 according to the second aspect of the invention, the air pump 316 has both the functions of the first air pump 114 and the second air pump 116 in the reprocessor 10 according to the first aspect of the invention.

The first basin 214a (second basin 214b) is provided at the interior with a forceps elevator port 124a (124b), a forceps port 126a (126b), an air/water supply port 128a (128b) and a suction port 130a (130b).

The first basin 214a also has formed at the interior thereof a detergent port 132a (132b), a disinfectant port 134a (134b) and a feedwater port 136a (136b). In addition, the floor 222 of the first basin 214a is provided at the lowest position thereof with a drain port 144a (144b).

In addition, the first basin 214a (214b) also has a circulation pump 182a (182b).

Moreover, as mentioned above, the first basin 214a has disposed therein blowing unit 270 (270RA, 270RB and 270RC (referred to collectively as 270R), and 270LA, 270LB and 270LC (referred to collectively as 270L)) for blowing air into the basin after the completion of each step.

As noted above, in the first basin 214a (second basin 214b), a total of six blowing unit 270 are arrayed in the direction of inclination of the floor 222, with three on the right side and three on left side. To simplify the diagram and make the illustrated arrangement easier to understand, these blowing unit are collectively represented in FIG. 17 as the right-side blowing unit 270R and the left-side blowing unit 270L.

The first basin 214a is also provided with a level sensor 142a (142b), a thermometer TE, and a heater H.

Each of the following is connected to both valves 160a and 162a (160b and 162b): the forceps elevator port 124a through a valve 150a (150b), the forceps port 126a through a valve 152a (152b), the air/water supply port 128a through a valve 154a (154b), the suction port 130a through a valve 156a (156b), the blowing unit 270R through a valve 400R, and the blowing unit 270L through a valve 400L. Moreover, as mentioned above, the reprocessor 210 has a valve 400 (400RA, 400RB, 400RC, 400LA, 400LB and 400LC) for each of the blowing unit 270. For the same reason as noted above, these valves are collectively represented in FIG. 17 as valves 400R and 400L.

The valves 150a, 152a, 154a, 156a, 400R and 400L are connected in parallel to a single line. The valves 160a and 162a are similarly connected in parallel to a single line.

The valves used in the endoscope reprocessor 210 are not subject to any particular limitation. Known valves capable of automatic opening and closing, such as solenoid valves and electrically operated valves, may be used.

The valve 160a (160b) is connected to the air pump 316.

In addition, the valve 162a (162b) is connected to a water supply line 164.

As shown in FIG. 17, the water supply line 164 has thereon a filter 166, a pressure-reducing valve 168, a first valve 170 and a second valve 172.

A line (water supply line 163a) from the above valve 162a is connected to the water supply line 164 at a point situated between the first valve 170 and the second valve 172. The water supply line 163a branches along the way, connecting to the subsequently described circulation pump 182a (182b) and the valve 180a (180b).

The second valve 172 is connected to the disinfectant tank 302 and a valve 198a (198b).

The detergent port 132a is connected through the valve 176a (176b) to the detergent pump 306. The disinfectant port 134a is connected through the valve 178a (178b) to the disinfectant pump 308. The feedwater port 136a is connected through the valve 180a (180b) to the water supply line 163a (163b).

The circulation pump 182a (182b) is connected to the first basin 214a (second basin 214b). This circulation pump 182a feeds liquid within the first basin 214 to a branch line which branches from the water supply line 163a and reaches the valve 180a (i.e., feedwater port 136a).

The drain port 144a is connected through the valve 190a (190b) to a discharge pump 318.

The water supply line 164 and the discharge line 194 are connected via a bypass valve 196 between a point upstream of the filter 166 on the water supply line 164 and a point upstream of the valve 192 on the discharge line 194.

The line between the drain port 144a and the valve 190a branches along the way, connecting through the valve 198a (198b) to the second valve 172 on the water supply line 164 and to the disinfectant tank 302.

In the endoscope reprocessor 210, the endoscope 250 is reprocessed by a cleaning and disinfecting process which basically entails carrying out the following steps in the indicated order: cleaning step→disinfecting step→rinsing step.

An example of the operations involved in reprocessing an endoscope 250 in the reprocessor 210 (cleaning and disinfecting process) is described below for the sake of illustration. The following description of endoscope reprocessing in the first basin 214a applies also to the second basin 214a, in which an endoscope is reprocessed in exactly the same way.

Because the individual steps of the endoscope 250 cleaning and disinfecting process carried out by the reprocessor 210 according to the second aspect of the invention shown in FIGS. 12A and 12B are basically the same as the individual steps of the endoscope 70 cleaning and disinfecting process carried out by the reprocessor 10 according to the first aspect of the invention shown in FIG. 1, the following description of endoscope 250 reprocessing by the reprocessor 210 emphasizes those features characteristic of and distinctive to the reprocessor 210 of the present embodiment while omitting detailed descriptions of components similar to those of the reprocessor 10 of the earlier described embodiment.

Also, as in the earlier description relating to the reprocessor 10 according to the first aspect of the invention, it should be noted that, in the description given below of the individual operations carried out in each step of the endoscope cleaning and disinfecting process, aside from those valves which are specifically mentioned as being open, all other valves are closed. Similarly, aside from those pumps which are mentioned as being activated, all other pumps are at rest.

First, the endoscope 250 is set by the operator at a predetermined position in the first basin 214a by positioning the control unit 256 with the engaging unit 234 and positioning the connector 256 with the engaging unit 236. In addition, the forceps elevator channel of the endoscope 250 is connected to the forceps elevator port 124a, the forceps channel is connected to the forceps port 126a, the air/water supply channel is connected to the air/water supply port 128a, and the suction channel is connected to the suction port 130a.

Connection between the respective ports and the respective channels of the endoscope 250 may be carried out by a known unit used in endoscope reprocessors, such as one involving the use of connectors or connecting tubes.

Once setting of the endoscope 250 in the first basin 214a is completed and an instruction to begin the cleaning process has been entered by the operator, the reprocessor 210 initially carries out a cleaning step in which liquid detergent is used to clean the endoscope 250, following which tap water is used to rinse the endoscope 250, and the detergent is removed.

First, the introduction of tap water is carried out. That is, a predetermined amount of tap water is introduced into the first basin 214a.

Next, once a predetermined amount of tap water has been introduced, detergent introduction is carried out. That is, a predetermined amount of liquid detergent is supplied to the interior of the first basin 214a. The introduction of tap water and the introduction of detergent may be carried out in parallel.

When predetermined amounts of tap water and detergent have been introduced into the first basin 214a, channel cleaning is carried out. That is, the detergent solution in the first basin 214a is circulated through the various channels of the endoscope 250, thereby successively cleaning each channel of the endoscope 250 with the detergent solution.

Once channel cleaning has been completed, an exterior flow cleaning operation is carried out. That is, the detergent solution within the first basin 214a is circulated over the exterior of the endoscope 250, thereby cleaning the exterior of the endoscope 250 with the detergent solution.

Once exterior flow cleaning has been carried out for a predetermined length of time, a cleaning discharge operation is carried out. That is, the valve 190a and the valve 192 are opened, the discharge pump 318 is activated, and the detergent solution within the first basin 214a is discharged.

After all of the detergent solution within the first basin 214a has been discharged, cleaning air supply is carried out. That is, air is supplied in turn to the respective channels of the endoscope 250 from the forceps elevator port 124a, the forceps port 126a, the air/water supply port 128a and the suction port 130a, thereby discharging from the endoscope any detergent solution remaining within the channels, and also discharging such detergent solution from the first basin 214a.

Once cleaning with the detergent solution has been completed, rinsing with tap water is carried out. In the second aspect of the invention, the water used for rinsing is not limited to tap water (this applies as well to the subsequently described rinsing step); for example, ion-exchanged water, deionized water or the like may be used.

Rinsing is basically carried out in the same way as cleaning with the detergent, except that detergent introduction into the first basin 214a is not carried out.

That is, first, tap water introduction is carried out.

Once a predetermined amount of tap water has been introduced into the first basin 214a, as in the above-described exterior flow cleaning operation, an exterior flow rinsing operation is carried out in which the exterior of the endoscope 250 is rinsed with tap water.

Once exterior flow rinsing has been completed, tap water is discharged from each channel and from the first basin 214a in the same way as in the cleaning air supply operation, thereby completing the washing step.

In the reprocessor 210, once the washing step has been completed, air is blown into the first basin 214a from blowing unit 270, thereby removing tap water adhering to/remaining on the basin inside walls, endoscope outer surface and lid underside.

That is, the air pump 316 is run with the valves 190a and 192 left open, along with which the valves 160a, 400RA and 400LA are opened, thereby blowing air into the first basin 214a from the topmost blowing unit 270RA and 270LA.

Next, the valves 400RA and 400LA are closed (or left open) and the valves 400RB and 400LB are opened, thereby blowing air into the first basin 214a from the intermediate blowing unit 270RB and 270LB.

Then, the valves 400RB and 400LB are closed (or left open) and the valves 400RC and 400LC are opened, thereby blowing air into the first basin 214a from the bottommost blowing unit 270RC and 270LC.

In this way, following completion of the washing step, tap water adhering to/remaining on the basin inside walls, endoscope outer surface and lid underside can be removed and discharged.

In the reprocessor 210, after the cleaning step has been completed and the subsequent blowing of air into the first basin 214a has been completed, a disinfecting step is then carried out in which the endoscope 250 is disinfected using disinfectant.

In the second aspect of the invention, by blowing air into the first basin 214a using blowing unit 270, tap water remaining on the basin inside walls and the endoscope outer surface is removed, thereby eliminating the need for a draining period. As a result, the time from the completion of the cleaning step to the start of the disinfecting step can be shortened. The same is true for the completion/start of the other steps.

In the disinfecting step, first, disinfectant introduction is carried out.

In the reprocessor 210, as mentioned above, by blowing air into the basin following completion of the cleaning step, tap water adhering to/remaining on the basin inside walls, endoscope outer surface and lid underside is removed, making it possible to advantageously suppress the dilution/degradation by tap water of the disinfectant introduced into first basin 214a. Therefore, according to the second aspect of the invention, proper disinfection of the endoscope 250 can be stably carried out with disinfectant that undergoes little degradation with repeated use of the disinfectant a given number of times.

Channel disinfection is carried out by introducing a predetermined amount of disinfectant into the first basin 214a. That is, the disinfectant within the first basin 214a is circulated through each channel of the endoscope 250, thereby successively disinfecting the respective channels of the endoscope 250 with the disinfectant.

Once channel disinfection has been completed, exterior flow disinfection in which the exterior of the endoscope 250 is disinfected with disinfectant is carried out.

Once exterior flow disinfection has been carried out for a given period of time, disinfectant recovery is carried out by opening the valve 198a connected to the drain port 144a and returning the disinfectant to the disinfectant tank 302.

When the disinfectant within the first basin 214a has been recovered to the disinfectant tank 302, a disinfecting air supply operation is carried out. That is, with the valve 198a remaining open, air supply to each channel of the endoscope 250 is carried out in the same way as in the above-described cleaning air supply operation.

This operation causes disinfectant remaining inside the channels to be discharged from the endoscope 250 so that disinfectant that remained within the channels is also recovered to the disinfectant tank 302, completing the disinfecting step.

In the reprocessor 210, once the disinfecting step has been completed, air is blown into the first basin 214a from blowing unit 270 in the same way as the air blowing operation at the completion of the above-described cleaning step, thereby removing and recovering to the disinfectant tank 250 any disinfectant attached to/remaining on the basin inside walls, endoscope outer surface and lid underside.

That is, with the valve 198a remaining open, in the same way as before, the air pump 316 is activated, the valves 160a, 400RA and 400LA are opened, and air is blown into the first basin 214a from the topmost blowing unit 270RA and 270LA. Next, the valves 400RB and 400LB are opened and air is blown into the first basin 214a from the intermediate blowing unit 270RB and 270LB, then the valves 400RC and 400 LC are opened and air is blown into the first basin 214a from the bottommost blowing unit 270RC and 270LC.

In this way, following completion of the disinfecting step, disinfectant adhering to/remaining on the basin inside walls, endoscope outer surface and lid underside can be removed and recovered to the disinfectant tank 302. Therefore, according to the second aspect of the invention, as mentioned above, degradation of the disinfectant can be suppressed, in addition to which a loss of disinfectant (wasteful consumption) can also be suppressed.

In the reprocessor 210, after the disinfecting step has been completed and the subsequent blowing of air into the first basin 214a has been completed, a rinsing step is then carried out in which the endoscope 250 is rinsed using tap water.

The rinsing step is basically carried out in the same way as rinsing with tap water in the above-described cleaning step. That is, first, tap water introduction is carried out.

Once tap water introduction has been completed, exterior flow rinsing is carried out in which the exterior of the endoscope 250 is rinsed with tap water.

When exterior flow rinsing has been completed, the valves 190a and 192 are opened, the discharge pump 318 is activated, and discharge in the rinsing step is carried out. Next, the valve 160a is opened and the air pump 316 is activated, along with which the valves 150a, 152a, 154a and 156a are each opened one at a time in this order, thereby carrying out air supply in the rinsing step and bringing the rinsing step to an end.

In the reprocessor 210, once the rinsing step has been completed, as with air blowing at the completion of the cleaning step described earlier, air is blown from the blowing unit 270 into the first basin 214a, thereby removing tap water adhering to/remaining on the basin inside walls, endoscope outer surface and lid underside.

That is, with the valves 190a and 192 remaining open, in the same way as before, the air pump 316 is activated, the valves 160a, 400RA and 400LA are opened, and air is blown into the first basin 214a from the topmost blowing unit 270RA and 270LA. Next, the valves 400RB and 400LB are opened and air is blown into the first basin 214a from the intermediate blowing unit 270RB and 270LB, then the valves 400RC and 400 LC are opened and air is blown into the first basin 214a from the bottommost blowing unit 270RC and 270LC.

In this way, following completion of the rinsing step, tap water adhering to/remaining on the basin inside walls, endoscope outer surface and lid underside can be removed and discharged.

With the completion of this rinsing step following the disinfecting step, the cleaning and disinfection of the endoscope 250 in the reprocessor 210 comes to an end. The operator is then alerted that reprocessing of the endoscope 250 is completed by a screen display, the generation of an audible signal or some other unit.

Here, in the reprocessor 210 according to the second aspect of the invention, following the rinsing step, i.e., following the completion of endoscope 250 reprocessing, because tap water adhering to/remaining on the reprocessor inside walls, endoscope outer surface and lid underside is removed by blowing air into the first basin 214a from the blowing unit 270, water can be prevented from dripping off the lid 220 when it is opened. Moreover, undesirable effects such as wetting of the reprocessor 210 vicinity from water drops adhering to the endoscope 250 can be successfully suppressed when the endoscope 250 is removed from the first basin 214a.

As mentioned above, in the reprocessor 210, numerous components, including tanks and pumps, are shared between the first basin 214a and the second basin 214b. However, aside from the supply lines for detergent, etc., the water supply line 164 and the discharge line 194, the two basins both have independent plumbing, thus making it possible for the same processing to be carried out at the same time in both basins 214a and 214b or for mutually different processing (asynchronous processing in both basins 214a and 214b) to be carried out at the same time.

In the reprocessor 210, fresh disinfectant is replenished to the disinfectant tank 302 by mounting disinfectant bottles B filled with liquid disinfectant on the mounts 302A.

According to one embodiment of the reprocessor 210, if the number of times the disinfectant is reused is set to a given number, once this number of endoscopes have been reprocessed, first, the valve 178a connected to the disinfectant port 136a is opened and the disinfectant pump 308 is activated, thereby introducing a predetermined amount of liquid disinfectant into the first basin 214a. Next, the valve 190a connected to the drain port 144a, the bypass valve 196, the pressure-reducing valve 168, the first valve 170 and the valve 180a connected to the feedwater port 136a are opened and the discharge pump 318 is activated, thereby circulating disinfectant over a path that includes the water supply line 164 and the discharge line 194. The interior of the reprocessor 210 is self-disinfected by this circulation.

Once disinfectant has been circulated on the above path which includes the water supply line 164 and the discharge line 194 for a given length of time, the valves 190a and 192 are opened and the discharge pump 318 is activated, thereby discharging the disinfectant. In addition, the valve 178a is opened and the disinfectant pump 308 is activated, thereby pouring all of the disinfectant remaining within the disinfectant tank 302 into the first basin 214a, then discharging it.

Once all of the disinfectant in the reprocessor 210 has been discharged, the pressure-reducing valve 168, the first valve 170 and the second valve 172 are opened, and a predetermined amount of tap water is poured into the disinfectant tank 302. The disinfectant bottles B are then mounted onto the two mounts 302A by the operator. The disinfectant is introduced gravitationally into the disinfectant tank 302, thereby replenishing the disinfectant tank 302 with fresh disinfectant.

In the reprocessor 210 according to the second aspect of the invention, as noted above, because air is blown from the blowing unit 270 into the basin 214 following the disinfecting step, there is little loss of disinfectant due to endoscope reprocessing. Therefore, compared with a conventional endoscope reprocessor, it is possible to reduce the amount of disinfectant that is replenished.

The reprocessor 210 shown in the diagrams has one detergent tank 300 and one disinfectant tank 302 for the two basins 214a and 214b, and likewise has one detergent pump 306 and one disinfectant pump. However, the second aspect of the invention is not limited in this regard.

For example, the endoscope reprocessor according to the second aspect of the invention may have two detergent tanks 300 and two disinfectant tanks 302, and may also have two detergent pumps 306 and two disinfectant pumps 308. In addition, with regard to the supply lines for these, the plumbing for the first basin 214a and the plumbing for second basin 214b may be completely independent. Alternatively, an arrangement in which a processing liquid is delivered to the two basins 214a and 214b with a single pump from two detergent tanks 300 (or from two disinfectant tanks 302) is also possible.

The endoscope reprocessor according to the second aspect of the invention is not limited to an arrangement having a floor 222 which is elongated and inclined as shown in the diagrams. The use of various other arrangements is also possible.

For example, the endoscope reprocessor may be one having an arrangement with a plurality of elongated basins which is exactly like the above-described reprocessor 210, except that the floor 222 in each basin is level rather than inclined.

Alternatively, the endoscope reprocessor may be one which, as described in above-cited JP 2006-68095 A, receives an endoscope 250 with the insertion tube 252 and the universal cord 254 thereof coiled, or may be an endoscope reprocessor which has an elongated cleaning tube for receiving the insertion tube 252 of an endoscope 250 and which receives and which cleans and disinfects within the basin portions of the endoscope 250 other than the insertion tube 252.

Also, the second aspect of the invention is not limited to arrangements which receive the endoscope 250 by loading on the floor (or a basket held in the basin), and may be employed in endoscope reprocessors of various types of arrangements.

Figure 18:
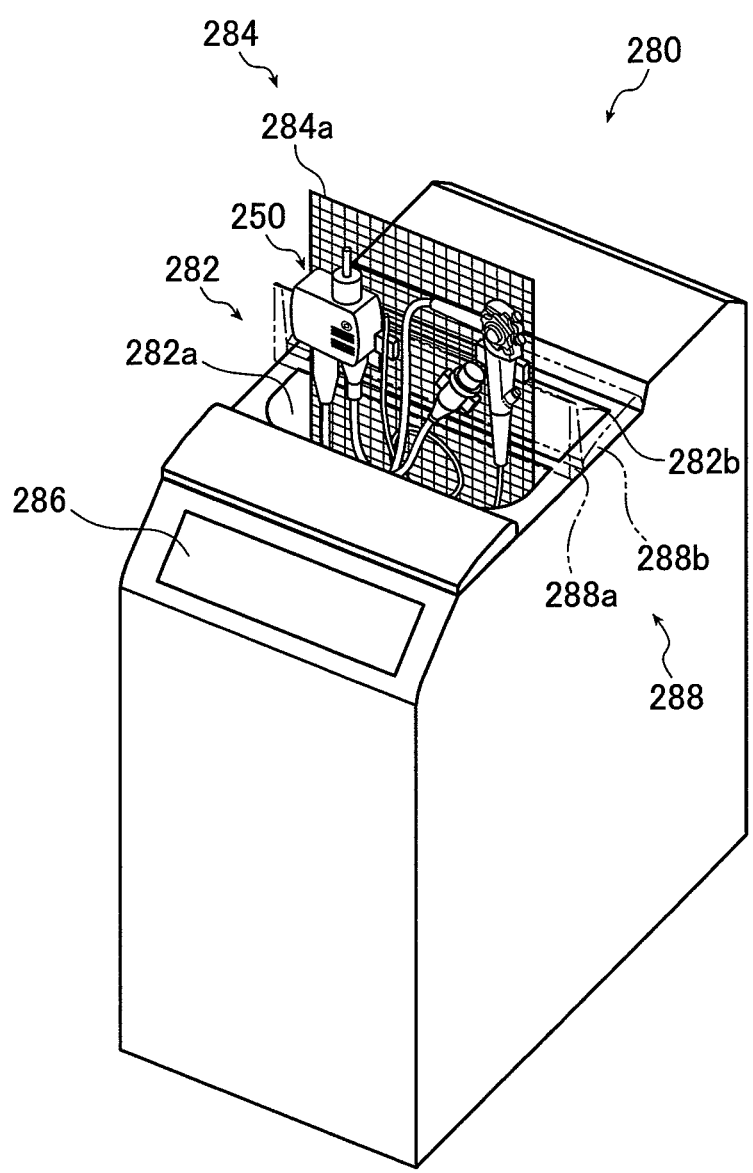
FIG. 18 is a schematic perspective view showing another embodiment of the endoscope reprocessor according to the second aspect of the invention.

For example, as in the case of the endoscope reprocessor 280 shown in FIGS. 18 and 19, the second aspect of the invention may also be advantageously used in a reprocessor 280 having a basin 282, a rack 284 which holds an endoscope 250 by locking (engaging) portions of the endoscope 250, and a raising and lowering unit for raising and lowering the rack so as to cause it to be received in or to emerge from the basin 282. This reprocessor 280 is an embodiment which combines the blowing unit of the endoscope reprocessor according to the second aspect of the invention with the endoscope reprocessor according to the earlier described first aspect of the invention.

Figure 19A:
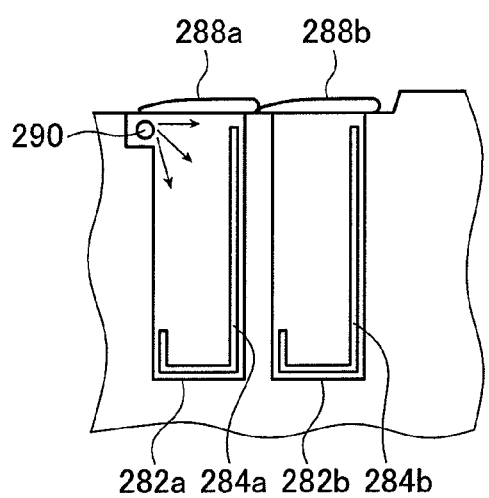
FIGS. 19A and 19B are schematic diagrams illustrating the operation of the endoscope reprocessor shown in FIG. 18.
Figure 19B:
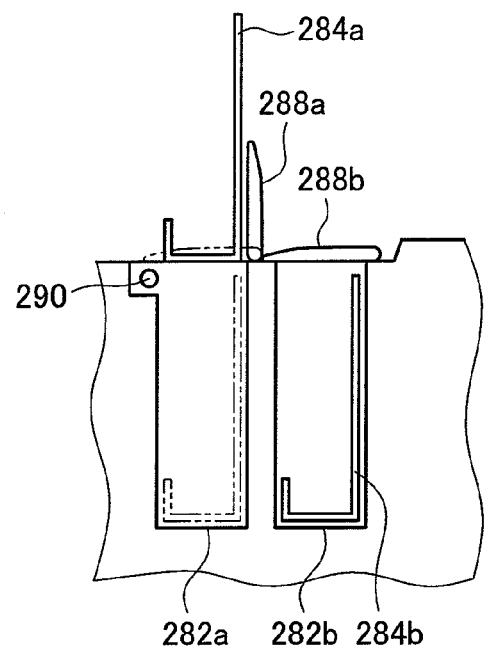

In the embodiment shown in FIGS. 18 and 19, two basins 282 (282a and 282b) are arranged front-to-back from the front surface (appearing on the left-hand side in FIGS. 19A and 19B) of the apparatus where the control panel 286 is located. Lids 288 (288a and 288b) are provided on the respective basins 282 so as to open and close the basins 282. In addition, each of the basins 282 is adapted to receive racks 284 (284a and 284b) each holding an endoscope 250.

The rack 284 is raised and lowered by a raising and lowering device (not shown), moving from a lowered position where it is fully received within the basin 282 as shown in FIG. 19A, to a raised position where it emerges from the basin 282 as shown in FIG. 19B. Moreover, the rack 284 is provided thereon with locking unit (omitted in the diagrams) for securing the control unit 256 and the connector 258 of the endoscope 250 and for securing also the insertion tube 252 and the universal cord 254, and thereby holding the endoscope 250 on the rack 284. In an alternative arrangement, use may simply be made of hooks or the like to secure the endoscope 250 and hold it on the rack 284. Any known unit may be used for raising and lowering the rack 284, such as a raising and lowering unit composed of a guide member for vertically guiding (in the raising and lowering direction) the rack 284 and a pulse motor for raising and lowering the rack 284.

A blowing unit 290 which blows air into the basin 282 is disposed near the top end of the interior front side of the basin 282.

In the reprocessor 280 shown in the diagrams, the blowing unit 290 is exemplified by having a length which, in the width direction of the reprocessor 280 (the direction perpendicular to the paper in FIG. 19), spans the full width of the rack 284 and blows air over this entire region. Alternatively, the blowing unit 290, as shown schematically by the arrows in FIG. 19A, may carry out, toward the top, middle and bottom of the rack 284, the blowing of air over the full width of the rack 284.

This blowing unit 290 may be any suitable known unit, such as an arrangement in which rows of air nozzles arranged in the lengthwise direction on the sidewall of an elongated tube connected to an air pump are provided in accordance with the directions in which air is to be blown (e.g., upward, center, downward).

In this reprocessor 280, first, as shown in FIG. 19B, the rack 284 is raised to a position where it emerges from the basin 282. In this position, the endoscope 250 is secured to the rack 284 and, in the manner previously described, the endoscope 250 is held on the rack 284 with each channel of the endoscope connected to a port.

Next, the rack 284 is lowered so that, as shown in FIG. 19A, the rack 284 and the endoscope 250 are received within the basin 282, and the lid 288 is closed.

In this state, as with the earlier described reprocessor 210, first a cleaning step is carried out in which the endoscope 250 is cleaned (cleaned with detergent and rinsed with tap water). Once the cleaning step has been completed, air is blown into the basin 214 from the blowing unit 290, thereby removing tap water remaining on the outer surface of the endoscope, the inside walls of the basin and the underside of the lid.

Then, a disinfecting step is carried out in which the endoscope 250 is disinfected with a disinfectant. Once the disinfecting step has been completed, air is similarly blown into the basin 214 from the blowing unit 290, thereby removing and recovering to the disinfectant tank any disinfectant remaining on the outer surface of the endoscope, the inside walls of the basin and the underside of the lid.

Once the disinfecting step and the blowing of air into the basin 282 have been completed, a rinsing step is carried out in which the endoscope 250 is rinsed with tap water.

When the rinsing step has been completed, air is blown into the basin 214 from the blowing unit 290, thereby removing tap water remaining on the endoscope outer surface, basin inside walls and lid underside. The blowing of air into the basin following completion of this rinsing step may be carried out with the rack 284 in the lowered state shown in FIG. 19A.

In the illustrated reprocessor 280 which raises and lowers the rack 284, once reprocessing has been completed, the rack 284 is raised by the raising and lowering unit and made to emerge from the basin 282, and the reprocessed endoscope 250 is removed. Accordingly, it is desirable for the blowing of air following the rinsing step to be carried out while the rack 284 is being raised. Because the vibrations transmitted to the endoscope 250 by raising the rack 284 also help to dislodge tap water from the endoscope outer surface and the like, the raising of the rack 284 in this way works together with the removal of tap water by the blowing of air to enable even more effective removal of tap water adhering to the endoscope outer surface. Therefore, by employing such an arrangement, the processing time can be shortened, in addition to which, as in the earlier described arrangement wherein air blowing is successively carried out from the topmost blowing unit 270 on the inclined floor, tap water adhering to the endoscope outer surface can be efficiently removed gravitationally.

In this reprocessor 280, the raising of the rack 284 following the end of endoscope 250 reprocessing may be carried out automatically when the cleaning and disinfecting process is over or may be carried out in accordance with instructions input by an operator.

It is desirable to alert the operator, such as by an audible signal, of the raising of the rack or the completion of rinsing (i.e., to prompt a rack raising instruction), when the rack 284 is raised automatically, before or after the start of such raising, and in cases where this is done in response to instructions entered by the operator, after the completion of the rinsing step.

The endoscope reprocessor according to the second aspect of the invention is basically configured as described above.

Although some aspects and embodiments of the endoscope reprocessor of the present invention have been described, those skilled in the art will appreciate that various modifications and changes may be made without departing from the spirit and scope of the invention as disclosed in the accompanying claims.

What is claimed is:

1. An endoscope reprocessor comprising:
   a basin for receiving an endoscope to be reprocessed;
   a rack which secures thereto a portion of the endoscope and moves vertically within the basin;
   a drive unit for vertically moving the rack, the drive unit comprising a motor capable of taking up a wire or letting the wire out to adjust the rack height in a vertical direction and a rack position sensor including a top dead center sensor and a bottom dead center sensor for detecting a rack position in the vertical direction;
   a positioning member for computing a stopping position target value of the rack and adjusting a rack stopping position when the endoscope is to be set on the rack by an operator;
   a drive control unit having a ROM which stores a correspondence relation between an operator's height and an optimal rack stopping position based on the operator's height, and information about a previous rack stopping position for the operator, the drive control unit computing an amount of rotation by the motor based on the rack position information detected by said top dead center sensor and said bottom dead center sensor and said stopping position target value, thereby moving the rack by rotating said motor for the computed amount of rotation; and
   a reading unit for reading information about the optimal rack stopping position for the operator, the operator's height data or an operator's identification number from an operator's IC tag;
   wherein the positioning member computes the stopping position target value of the rack based on the information about the optimal rack stopping position for the operator read by the reading unit or set according to the operator's height data read by the reading unit and the correspondence relation stored in the ROM, or the information about the previous rack stopping position for the operator retrieved from the ROM based on the operator's identification number read by the reading unit to adjust the rack stopping position in accordance with the operator when the endoscope is to be set on the rack by the operator.

2. The endoscope reprocessor of claim 1, wherein the basin has a horizontal cross-section which is rectangular and has a vertical height which is greater than a length of the horizontal cross-section in a lengthwise direction thereof.

3. The endoscope reprocessor of claim 1, wherein the reading unit communicates wirelessly with the IC tag and reads the information about the optimal rack stopping position for the operator, the operator's height data, or the operator's identification number.

4. The endoscope reprocessor of claim 1, wherein the drive unit tilts the rack to a predetermined angle at the rack stopping position.

5. The endoscope reprocessor of claim 1, wherein the rack secures the endoscope thereto at a plurality of places.

6. The endoscope reprocessor of claim 1, wherein the rack has locking members which respectively secure thereto a connector and a control unit of the endoscope.

7. The endoscope reprocessor of claim 6, wherein the rack additionally has a locking member which secures thereto an insertion tube of the endoscope.

8. The endoscope reprocessor of claim 1, further comprising, in addition to said basin, at least one additional basin of the same construction, wherein said at least one additional basin has a horizontal cross-section which is rectangular and said basin and said at least one additional basin are arranged in parallel with long sides of the respective rectangular cross-sections thereof facing frontally so as to be mutually adjacent.

9. The endoscope reprocessor of claim 1, wherein the rack is composed of a plate portion having a shape which runs parallel to a control face of the basin, the operator facing to and working on the control face, and is disposed along a far side face from said control face, a bottom portion which is situated at a lower end of said plate portion in a perpendicular direction, and an upturned portion which is parallel to said plate portion and disposed on the control face side of said basin, wherein said plate portion is provided with two sets of locking members for securing various portions of the endoscope, the locking members being respectively disposed at symmetric positions.

* * * * *